(12) United States Patent
Sano et al.

(10) Patent No.: US 12,171,532 B2
(45) Date of Patent: Dec. 24, 2024

(54) ELECTRONIC VALVE, SPHYGMOMANOMETER, AND APPARATUS

(71) Applicant: OMRON HEALTHCARE CO., LTD., Muko (JP)

(72) Inventors: Yoshihiko Sano, Kyoto (JP); Takanori Nishioka, Kyoto (JP); Hirofumi Onohara, Tokyo (JP); Gaku Kubota, Tokyo (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 907 days.

(21) Appl. No.: 16/942,845

(22) Filed: Jul. 30, 2020

(65) Prior Publication Data

US 2020/0352454 A1 Nov. 12, 2020

Related U.S. Application Data

(63) Continuation of application No. PCT/JP2019/002310, filed on Jan. 24, 2019.

(30) Foreign Application Priority Data

Feb. 13, 2018 (JP) ................................. 2018-023421

(51) Int. Cl.
*A61B 5/0235* (2006.01)
*A61B 5/021* (2006.01)
(Continued)

(52) U.S. Cl.
CPC ........ *A61B 5/0235* (2013.01); *A61B 5/02141* (2013.01); *A61B 5/0225* (2013.01);
(Continued)

(58) Field of Classification Search
CPC . A61B 5/0235; A61B 5/02141; A61B 5/0225; A61B 2562/0247; F16K 31/0651; F16K 31/0655; F16K 31/0672
(Continued)

(56) References Cited

U.S. PATENT DOCUMENTS 3,433,256 A 3/1969 Stillhard et al.
4,848,727 A 7/1989 Nanbu et al.
(Continued)

FOREIGN PATENT DOCUMENTS

GB 1164043 A 9/1969
GB 2 201 232 A 8/1988
(Continued)

OTHER PUBLICATIONS

Sep. 24, 2021 Office Action issued in Chinese Patent Application No. 201980013083.9.
(Continued)

*Primary Examiner* — Eric F Winakur
*Assistant Examiner* — Abid A Mustansir
(74) *Attorney, Agent, or Firm* — Oliff PLC

(57) ABSTRACT

An electronic valve with: a yoke including an end plate portion and a side plate portion; a pole piece; a solenoid coil; and a diaphragm made of a plate-shaped magnetic material. The pole piece has an opening at one end portion and a first fluid inlet/outlet communicating with the opening at the other end portion. A biasing unit biases the diaphragm in a direction away from one end portion of the pole piece in a manner of moving the diaphragm translationally in one direction. In a non-operating time, the electronic valve comes into an open state where the opening is open. In an operating time, the diaphragm approaches the one end portion of the pole piece against the biasing force of the biasing unit by a magnetic force generated by the solenoid
(Continued)

coil, and the electronic valve can come into a closed state where the opening is closed.

9 Claims, 12 Drawing Sheets

(51) Int. Cl.
*A61B 5/0225* (2006.01)
*F16K 31/06* (2006.01)

(52) U.S. Cl.
CPC ...... *F16K 31/0651* (2013.01); *F16K 31/0655* (2013.01); *A61B 2562/0247* (2013.01)

(58) Field of Classification Search
USPC ..................................................... 251/129.16
See application file for complete search history.

(56) References Cited

U.S. PATENT DOCUMENTS

| | | | | | |
|---|---|---|---|---|---|
| 4,858,886 | A | * | 8/1989 | Tatara | .................... F02M 23/04 251/129.17 |
| 2001/0051773 | A1 | * | 12/2001 | Oka | ..................... A61B 5/0225 600/490 |
| 2002/0002340 | A1 | * | 1/2002 | Nishibayashi | ..... A61B 5/02225 600/494 |
| 2002/0013533 | A1 | * | 1/2002 | Oka | ................... A61B 5/02405 600/481 |
| 2004/0046137 | A1 | * | 3/2004 | Herbert | ................... F16K 37/00 251/129.17 |
| 2007/0208258 | A1 | * | 9/2007 | Whitaker | ............... A61B 5/021 600/490 |
| 2009/0062663 | A1 | * | 3/2009 | Friedman | ............... A61B 5/022 600/496 |

FOREIGN PATENT DOCUMENTS

| | | |
|---|---|---|
| JP | H08-203730 A | 8/1996 |
| JP | 2006-242232 A | 9/2006 |
| JP | 2008-005926 A | 1/2008 |
| JP | 2016-138573 A | 8/2016 |

OTHER PUBLICATIONS

Apr. 23, 2019 International Search Report issued in International Patent Application No. PCT/JP2019/002310.

* cited by examiner

OPEN STATE (WHEN UNPOWERED)

CLOSED STATE (WHEN POWERED)

ELECTRONIC VALVE, SPHYGMOMANOMETER, AND APPARATUS

CROSS-REFERENCE TO RELATED APPLICATION

This is a continuation application of International Application No. PCT/JP2019/002310, with an International filing date of Jan. 24, 2019, which claims priority of Japanese Patent Application No. 2018-023421 filed on Feb. 13, 2018, the entire content of which is hereby incorporated by reference.

TECHNICAL FIELD

The present invention relates to an electronic valve, and more particularly to an electronic valve that is opened and closed by a magnetic force of a solenoid coil. The present invention also relates to a sphygmomanometer and an apparatus having such an electronic valve.

BACKGROUND ART

Conventionally, as an electronic valve used for a sphygmomanometer, there has been known an electronic valve disclosed in, for example, Patent Literature 1 (Japanese Patent Laid-open Publication No. 08-203730). The electronic valve includes a U-shaped frame and a yoke mounted to close the open end of the frame. A substantially cylindrical coil bobbin (coil frame) and a solenoid coil wound around the coil bobbin are housed therein. Further, a rod-shaped movable iron core is slidably inserted in the coil bobbin. A fixed iron core provided with a flow port through which fluid flows is disposed on the bottom plate of the frame facing the yoke. One end of the movable iron core faces the flow port of the fixed iron core. In a non-operating time when the solenoid coil is in an unpowered state, one end of the movable iron core is separated from the flow port of the fixed iron core by a biasing force of a spring. In an operating time when the solenoid coil is in a powered state, the movable iron core is moved in the coil bobbin against the biasing force of the spring by the magnetic force generated by the solenoid coil, and one end of the movable iron core closes the flow port of the fixed iron core. Thereby, the electronic valve is opened and closed.

SUMMARY OF INVENTION

Meanwhile, there is a growing need for measuring blood pressure with a sphygmomanometer always attached to the wrist like a wristwatch due to the recent health-oriented boom. In this instance, it is desirable to reduce the size of components such as an electronic valve as much as possible.

However, in a general electronic valve disclosed in Patent Literature 1, there is a problem that the size (in particular, the size along the longitudinal direction of the movable iron core) of the electronic valve increases because the movable iron core is rod-shaped and moves along its longitudinal direction.

Therefore, it is an object of the present invention to provide an electronic valve that can be formed in small size. It is another object of the present invention to provide a sphygmomanometer and apparatus including such an electronic valve.

In order to achieve the above object, an electronic valve according to the present disclosure is an electronic valve that permits or blocks a flow of fluid, the electronic valve comprising:

a yoke including an end plate portion having an annular peripheral edge, and a side plate portion connected to the peripheral edge of the end plate portion and annularly surrounding a space adjacent to one side of the end plate portion;

a pole piece orthogonal to the end plate portion of the yoke and extending in one direction from one end portion existing in the space of the one side to other end portion of opposite side, the pole piece having an opening at the one end portion and having, at the other end portion, a first fluid inlet/outlet in communication with the opening through an inside of the pole piece;

a solenoid coil housed in an annular space between the pole piece and the side plate portion of the yoke;

a diaphragm made of a disk-shaped magnetic material that faces the end plate portion of the yoke via the space and has a dimension extending over the annular edge of the side plate portion of the yoke;

a coil spring that biases the diaphragm in a direction away from the one end portion of the pole piece in a manner of moving the diaphragm translationally in the one direction; and a casing that collectively covers the yoke, a portion of the pole piece extending into the space of the one side, the solenoid coil, the diaphragm, and the coil spring, with the other end portion of the pole piece exposed to an outside, wherein the coil spring is disposed along an annular space between the side plate portion of the yoke and an annular outer peripheral wall of the casing facing the side plate portion, and is in annular contact with a peripheral edge portion of a surface of the diaphragm facing the end plate portion, a gap in a radial direction is provided between the annular outer peripheral wall of the casing and the peripheral edge portion of the diaphragm, an elastic body for closing the opening is integrally attached to a portion of the diaphragm facing the opening at the one end portion of the pole piece, and the elastic body has a flat end face projecting in a columnar shape from the diaphragm toward the opening at the one end, the pole piece has, at the one end portion, a recess having a flat bottom opened toward the elastic body attached to the diaphragm, and the opening is opened at the bottom of the recess, in a non-operating time when the solenoid coil is in an unpowered state, the diaphragm is separated from the one end portion of the pole piece by a biasing force of the coil spring, causing the end face of the elastic body being separated from the opening, such that the electronic valve comes into an open state where the opening is opened, and in an operating time when the solenoid coil is in a powered state, the diaphragm approaches the one end portion of the pole piece against the biasing force of the coil spring by a magnetic force generated by the solenoid coil, such that the electronic valve is able to come into a closed state where the opening is closed with the end face of the elastic body.

In the present specification, a "yoke" and a "pole piece" are elements each serving to guide magnetic lines of force as is known in the field of electromagnets, and are each made of a magnetic material (in particular, ferromagnetic materials such as iron are preferred.).

The peripheral edge of the end plate portion of the yoke widely includes an annular shape such as a circular shape or a round square (rounded square) shape. This also applies to the annular shape of the side plate portion of the yoke.

The "annular edge" of the side plate portion of the yoke refers to the edge on the opposite side to the end plate portion.

The "other end" of the pole piece may project from the end plate portion of the yoke or may stop on an outer surface of the end plate portion (the surface facing the opposite side to the space of the one side out of the two surfaces of the end plate portion).

In the present specification, the "elastic body" refers to an object made of an elastic material (flexible material), such as silicone rubber, nitrile rubber (NBR), or ethylene propylene diene rubber (EPDM).

As an open/closed state of the valve, an intermediate state exists between the closed state and the open state in which a flow rate is controlled in accordance with the powered amount of the solenoid.

In another aspect, a sphygmomanometer of the present disclosure is a sphygmomanometer that measures blood pressure of a part to be measured, the sphygmomanometer comprising:
 a body;
 a cuff attached to the part to be measured;
 a pump mounted in the body and configured to supply fluid to the cuff through a flow path;
 the electronic valve according to an electronic valve as described above, mounted in the body and interposed between the pump or the flow path and an atmosphere;
 a pressure control unit that controls pressure of the cuff by supplying the fluid to the cuff through the flow path with the pump and/or discharging the fluid from the cuff through the electronic valve; and
 a blood pressure calculation unit that calculates the blood pressure based on pressure of the fluid stored in the cuff.

In yet another aspect, an apparatus of the present disclosure is an apparatus capable of measuring blood pressure of a part to be measured, the apparatus comprising:
 a body;
 a cuff attached to the part to be measured;
 a pump mounted in the body and configured to supply fluid to the cuff;
 the electronic valve according to an electronic valve as described above, mounted in the body;
 a pressure control unit that controls pressure of the cuff by supplying the fluid to the cuff through the electronic valve with the pump and/or discharging the fluid from the cuff; and
 a blood pressure calculation unit that calculates the blood pressure based on pressure of the fluid stored in the cuff.

BRIEF DESCRIPTION OF DRAWINGS

The present invention will become more fully understood from the detailed description given hereinbelow and the accompanying drawings which are given by way of illustration only, and thus are not limitative of the present invention, and wherein.

DESCRIPTION OF EMBODIMENTS

Hereinafter, embodiments of the present invention will be described in detail with reference to the drawings.

Figure 1:
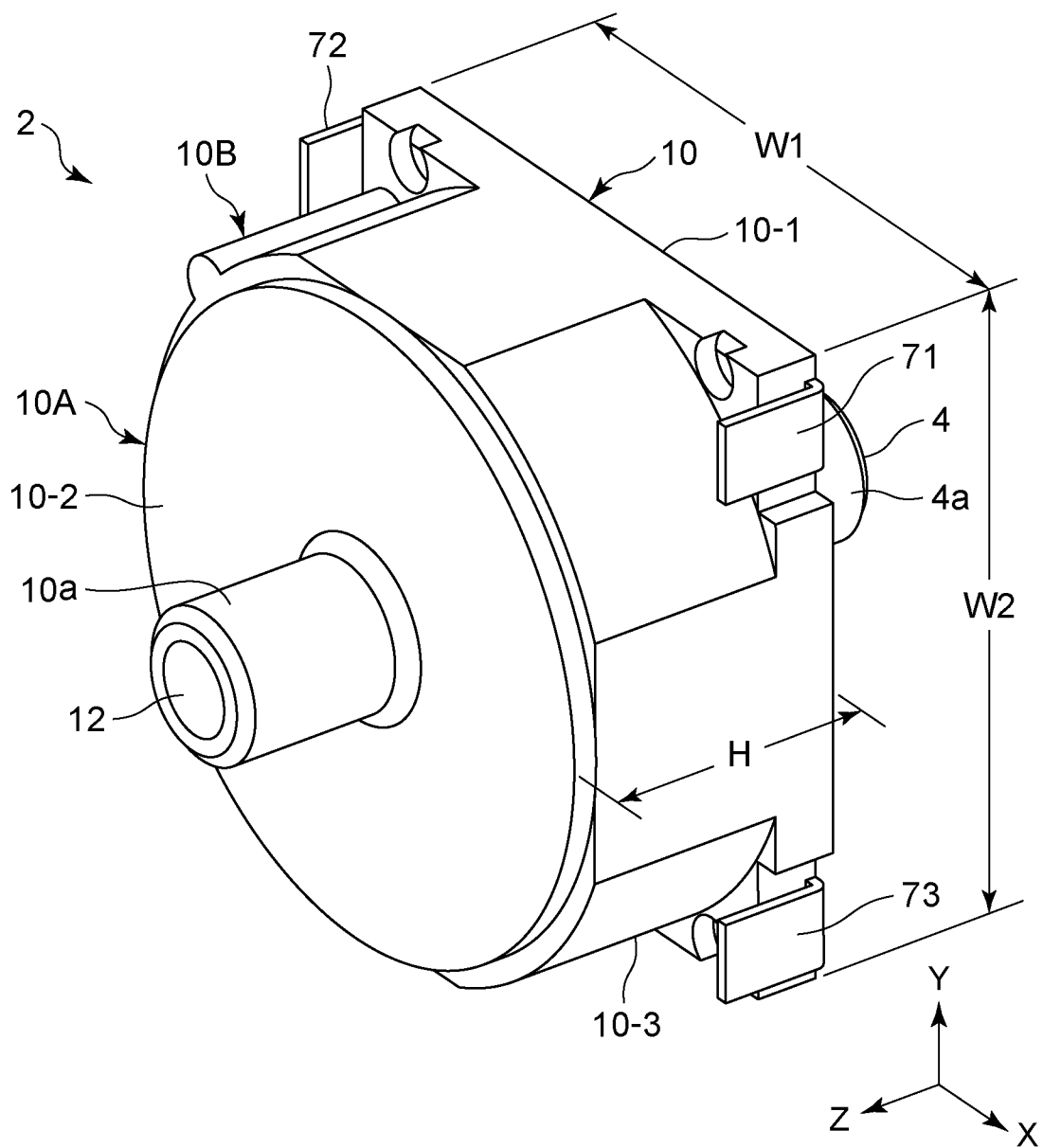
FIG. 1 is a perspective view illustrating an external view of an electronic valve according to an embodiment of the present invention.
Figure 2:
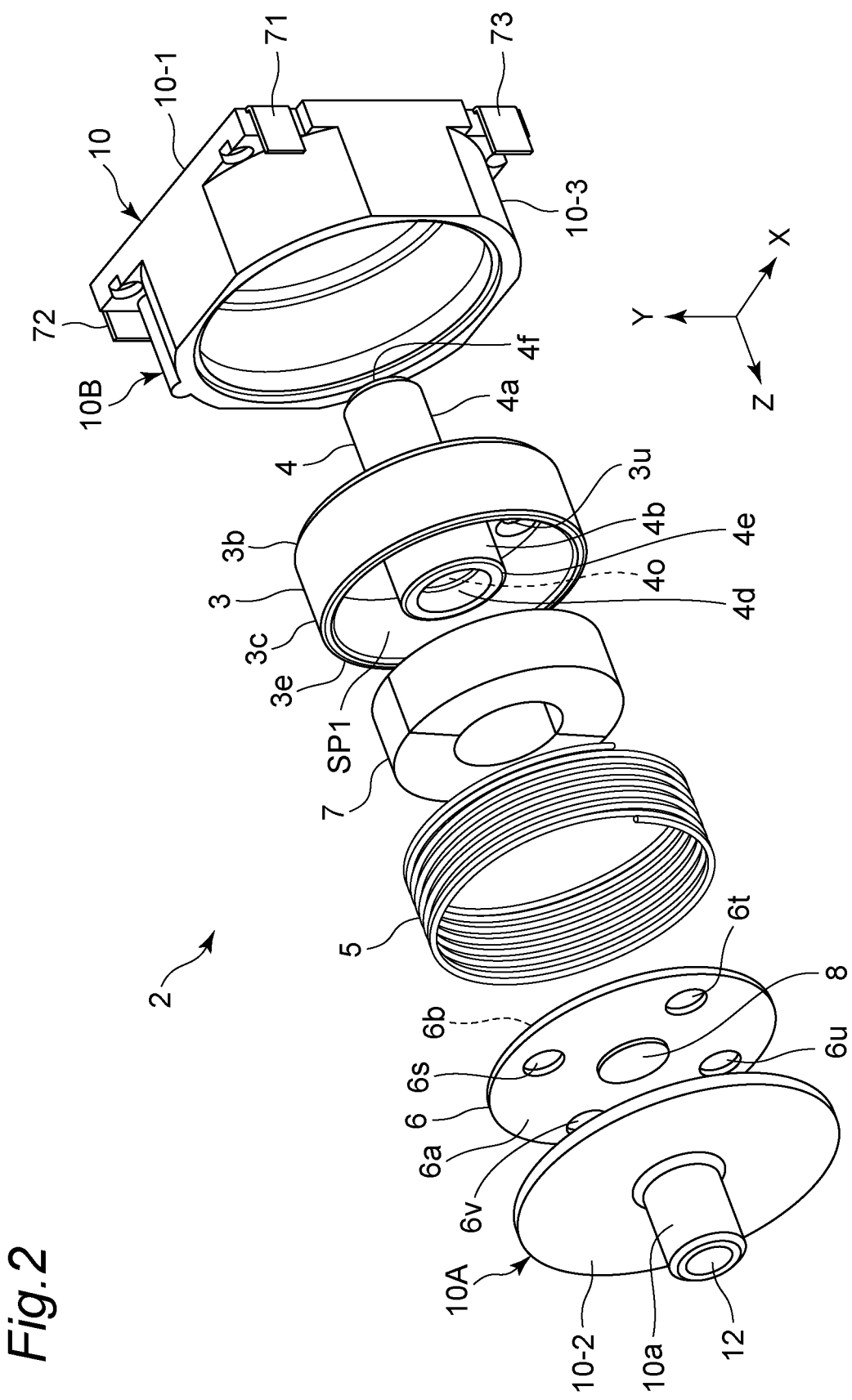
FIG. 2 is a view illustrating the electronic valve when viewed obliquely in a disassembled state.
Figure 3:
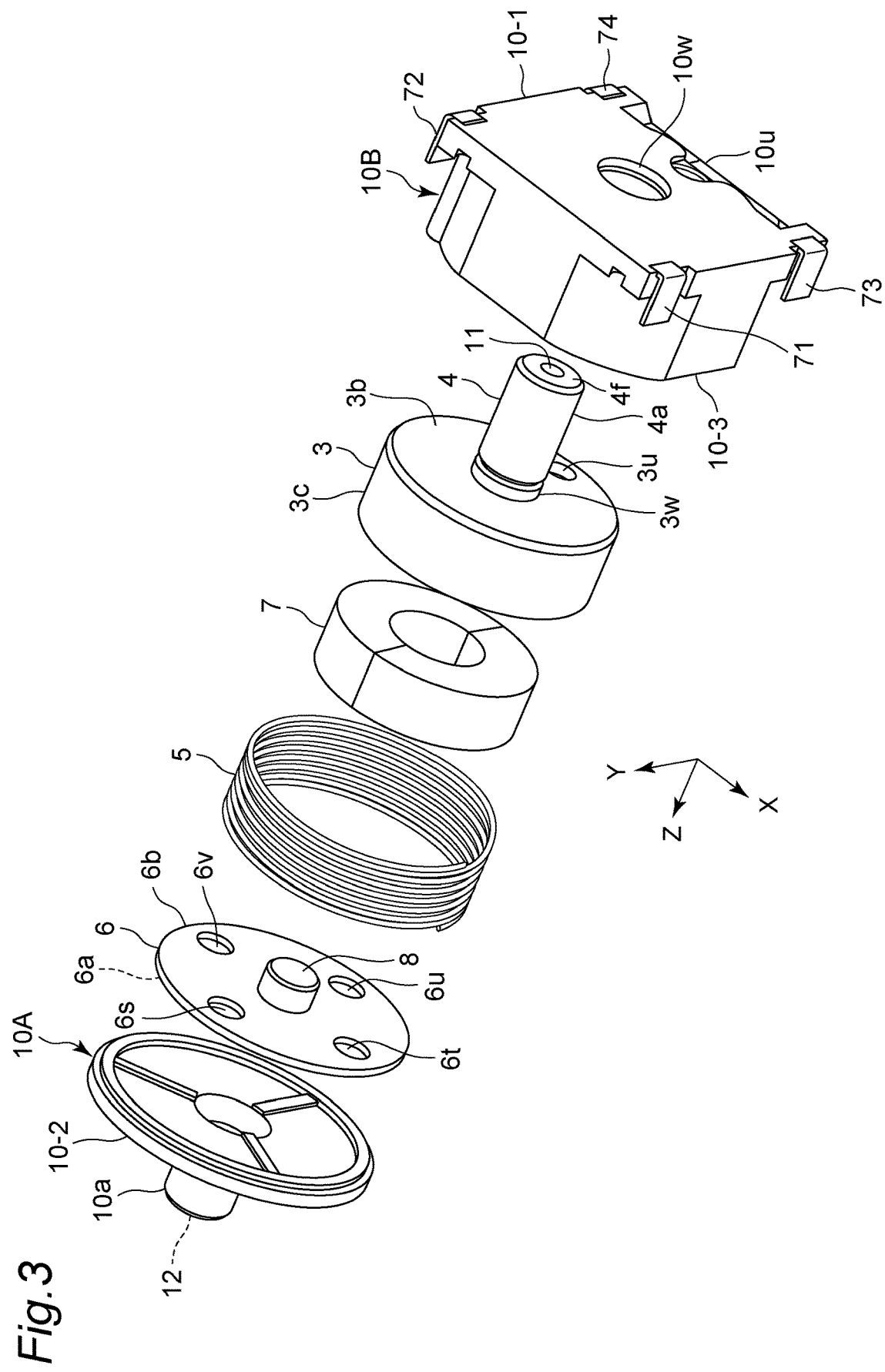
FIG. 3 is a view illustrating the object of FIG. 2 viewed from another direction.

FIG. 1 illustrates an external view of an electronic valve (the whole is denoted by reference numeral 2) according to an embodiment of the present invention when viewed obliquely. FIG. 2 illustrates the electronic valve 2 in a disassembled state. FIG. 3 illustrates another view of the object of FIG. 2. For the ease of understanding, FIGS. 1 to 3 and FIGS. 4 to 7 and FIGS. 11 to 12, which will be described later, also illustrate XYZ Cartesian coordinates. Hereinafter, for convenience, the Z direction may be referred to as a thickness direction, and the XY direction may be referred to as a plane direction.

Configuration of Electronic Valve

As can be seen from FIG. 1, the electronic valve 2 includes a case 10 as a casing. The case 10 includes a lid case 10A disposed on one side (+Z side) in the thickness direction, and a main case 10B disposed on the opposite side (−Z side) in the thickness direction. In this example, the lid case 10A has a disk-shaped second end wall 10-2 forming an outer wall, and a cylindrical portion 10a (forming a second fluid inlet/outlet 12 for allowing fluid to pass) projecting to the outside (+Z side) from the center of the second end wall 10. The main case 10B has a rectangular (square in this example) plate-shaped first end wall 10-1, and a substantially cylindrical outer peripheral wall 10-3 continuous to the first end wall 10-1. As illustrated in FIG. 3, a through hole 10w into which a pole piece 4 to be described later is fitted is provided in the center of the first end wall 10-1. One side (the side on the −Y side in this example) of the first end wall 10-1 is provided with a through hole 10u through which wiring (lead wires not illustrated) passes. Connection terminals 71, 72, 73, 74 (references) made of metal (copper, etc.) are integrally provided at four corners of the outer surface of the first end wall 10-1.

In this case, the lid case 10A is formed by integrally molding a non-magnetic plastic material. The main case 10B is formed by integrally molding (insert molding) a non-magnetic plastic material together with the connection terminals 71, 72, 73, 74. In this example, the second end wall 10-2 of the lid case 10A is welded to the outer peripheral wall 10-3 of the main case 10B. However, the present invention is not limited thereto, but the second end wall 10-2 may be screwed onto the outer peripheral wall 10-3.

As can be seen from FIGS. 2 and 3, inside a case 10 of the electronic valve 2, there are provided a yoke 3, a pole piece 4 integrally attached orthogonally to (an end plate portion 3b of) the yoke 3, a solenoid coil 7, a coil spring 5 as a biasing unit, a diaphragm 6, and an elastic body 8 integrally formed with the diaphragm 6.

As illustrated in FIG. 2, the yoke 3 includes an end plate portion 3b having an annular (a circle in this example) peripheral edge, and a side plate portion 3c connected to the peripheral edge of the end plate portion 3b and annularly surrounding a space SP1 adjacent to one side (+Z side) of the end plate portion 3b. As illustrated in FIG. 3, a through hole 3w is formed in the center of the end plate portion 3b, and the pole piece 4 is fitted into the through hole 3w. A through hole 3u through which wiring (lead wires not illustrated) is passed is provided in a portion corresponding to the through hole 10u of the first end wall 10-1 of the main case 10B out of the peripheral edge portion of the end plate portion 3b. Note that the shape of the peripheral edge of the end plate portion 3b of the yoke 3 is not limited to a circular shape but may be a round square (rounded square) shape. This also applies to the annular shape of the side wall portion of the side plate portion 3c.

In this example, an outer diameter of the side plate portion 3c of the yoke 3 is set smaller than an inner diameter of the outer peripheral wall 10-3 of the main case 10B. Thus, in an assembled state illustrated in FIG. 4, an annular space SP2 for housing the coil spring 5 is formed between the side plate portion 3c of the yoke 3 and the outer peripheral wall 10-3 of the main case 10B.

As can be seen from FIGS. 2 and 3, the pole piece 4 has a substantially cylindrical shape as a whole. The pole piece 4 includes a projection 4a which is fitted into the through hole 3w of the yoke 3 in the axial direction (Z direction) and projects to the outside, and a main portion 4b having an outer diameter larger than the outer diameter of the projection 4a. That is, the pole piece 4 extends in one direction (Z direction) from one end portion 4e existing in the space SP1 on one side (+Z side) to the other end portion 4f on the opposite side (−Z side), perpendicular to the end plate portion 3b of the yoke 3. In this example, the pole piece 4 has a recess 4d in a circular plane shape opened toward the elastic body 8 of the diaphragm 6 at the one end portion 4e. This recess 4d has a flat bottom 4d1. A circular opening 4o is opened at the bottom 4d1 of the recess 4d. A circular first fluid inlet/outlet 11 communicating with the opening 4o through the inside of the pole piece 4 is provided at the other end portion 4f of the pole piece 4.

In this example, the yoke 3 and the pole piece 4 are each made of SUM 24L (sulfur composite free-cutting steel) that is a magnetic material. In this example, the projection 4a of the pole piece 4 is press-fitted into the through hole 3w of the yoke 3, and the yoke 3 and the pole piece 4 are configured integrally. Thereby, the magnetic resistance between the pole piece 4 and the yoke 3 is small, and the efficiency of a magnetic circuit passing through the pole piece 4 and the yoke 3 is improved. Air leakage can be prevented by improving airtightness between the pole piece 4 and the yoke 3. Note that the yoke 3 and the pole piece 4 may be formed as a spatially continuous integral body.

As can be seen from FIGS. 2 and 3, the solenoid coil 7 has a cylindrical outer shape with a thickness of pressure. The dimension of the solenoid coil 7 is set so as to be housed in the annular space SP1 between the pole piece 4 and the side plate portion 3c of the yoke 3. A pair of lead wires (not illustrated) extend from the solenoid coil 7.

Figure 4:
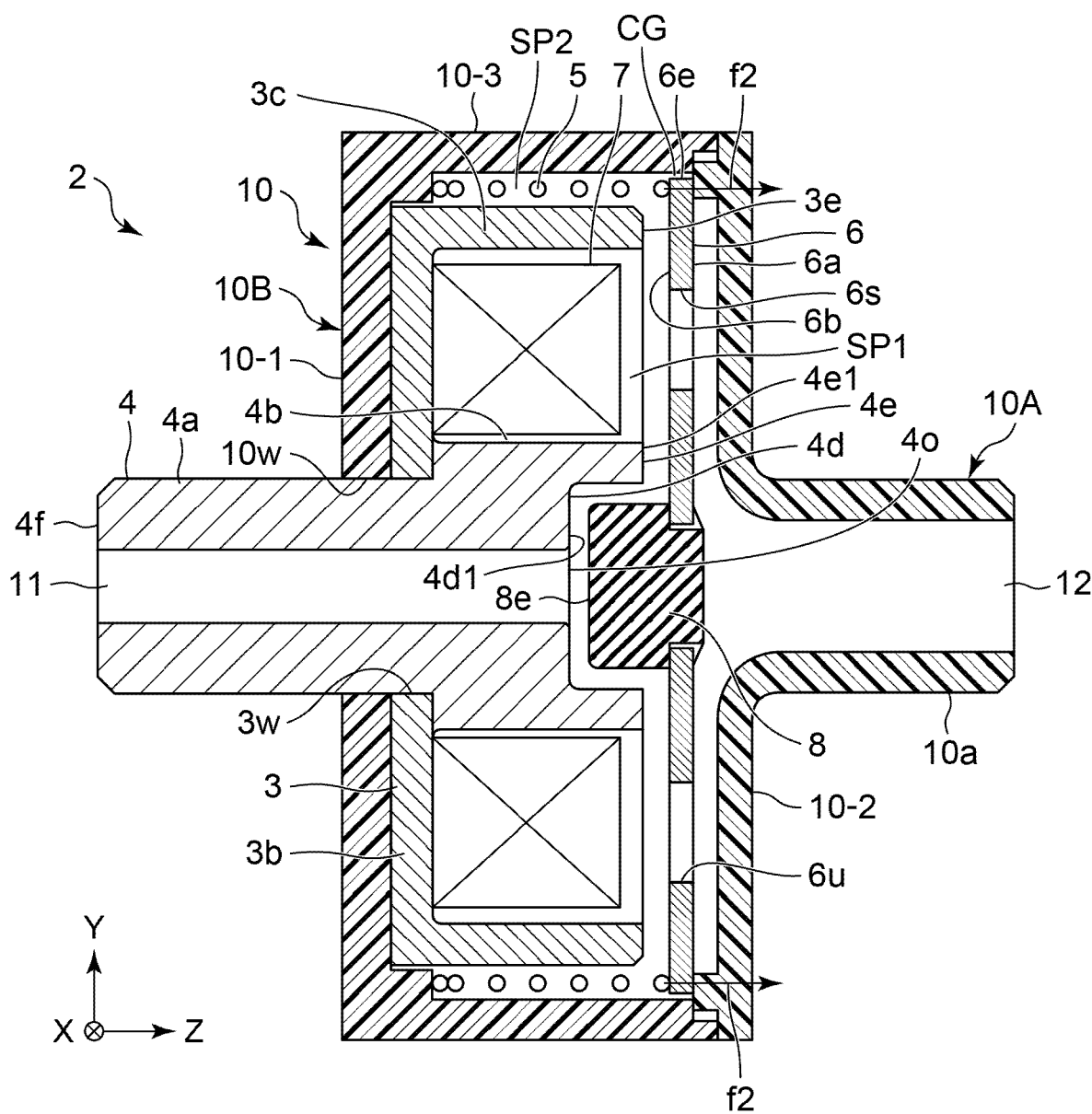
FIG. 4 is a view illustrating an example of a cross-sectional structure when the electronic valve is cut in a plane including fluid inlet/outlets.
Figure 5:
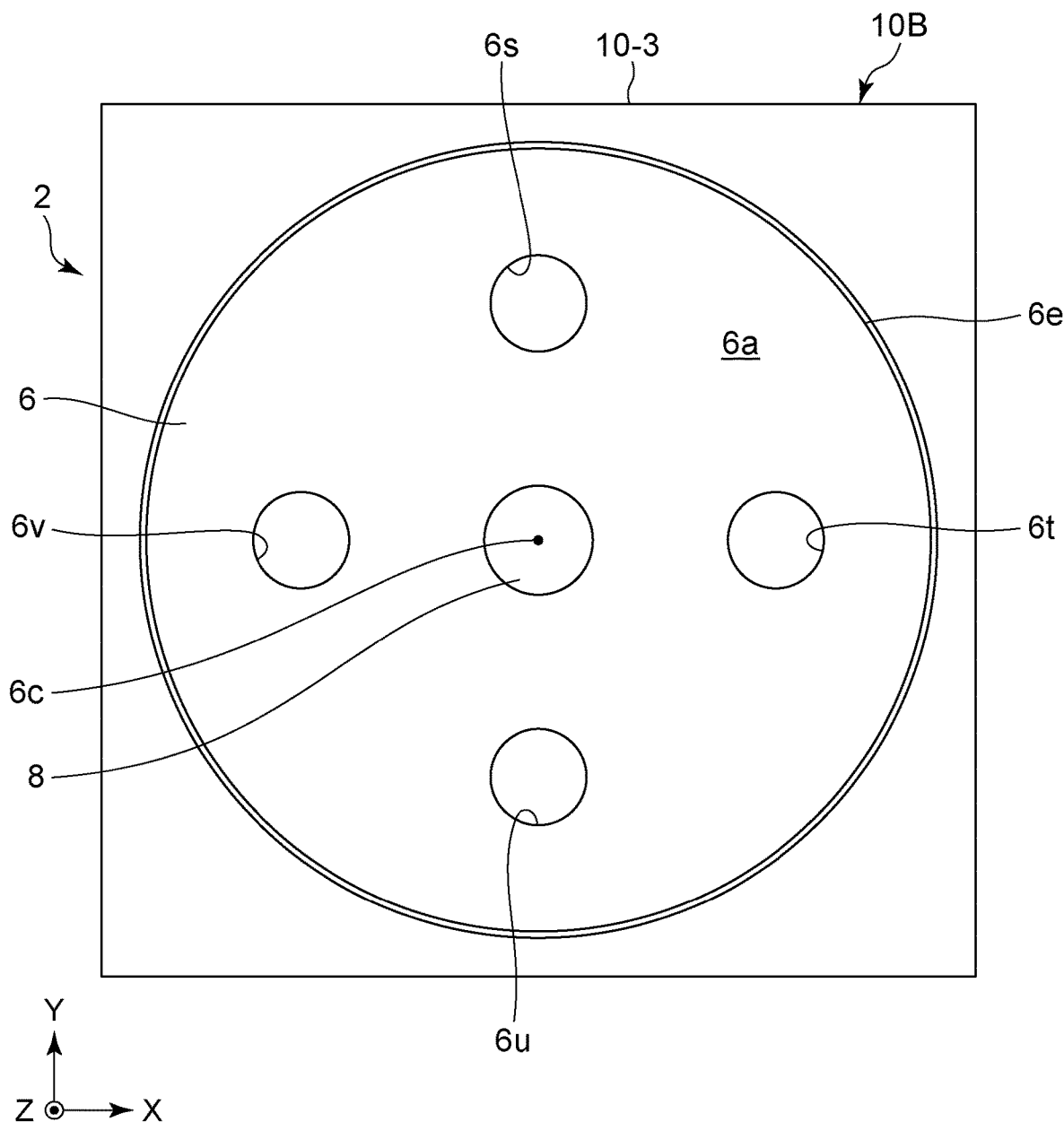
FIG. 5 is a view illustrating a plane shape of a diaphragm provided in a case of the electronic valve.

The coil spring 5 has a substantially cylindrical contour. In the assembled state illustrated in FIG. 4, the coil spring 5 is disposed along the annular space SP2 between the side plate portion 3c of the yoke 3 and the outer peripheral wall 10-3 of the main case 10B, and in annular contact with a peripheral edge portion of the surface 6b of the diaphragm 6 facing the end plate portion 3b. Thus, the coil spring 5 biases the diaphragm 6 in a direction (i.e., the +Z direction) separating from the one end portion 4e of the pole piece 4 in a manner of moving the diaphragm 6 translationally in one direction (Z direction). In FIG. 4, a biasing force f2 by which the coil spring 5 biases the diaphragm 6 is schematically illustrated by an arrow. The biasing unit can be easily made of a small number of components (i.e., coil spring 5).

As can be seen from FIGS. 2 and 3, the diaphragm 6 has a substantially disk-shaped outer shape. In this example, as can be seen from FIG. 5 (illustrating the planar shape of the diaphragm 6), four circular through holes 6s, 6t, 6u, 6v are provided between a center 6c and a peripheral edge portion 6e in the radial direction of the diaphragm 6 and at an equal angular pitch (a pitch of 90° in this example) in the circumferential direction. This enables the fluid to flow through the through holes 6s, 6t, 6u, 6v between the rear surface (a face facing the +Z side) 6a side and the inner surface (a face facing the −Z side) 6b side of the diaphragm 6.

As can be seen from FIG. 4, the diaphragm 6 has a dimension extending over an annular edge 3e of the side plate portion 3c of the yoke 3. As a result, the outer diameter of the diaphragm 6 is substantially equal to the outer diameter of the coil spring 5. A slight gap CG in the radial direction is provided between the outer diameter of the diaphragm 6 and the inner diameter of the outer peripheral wall 10-3 of the main case 10B so that the diaphragm 6 can move translationally in one direction (Z direction) within the outer peripheral wall 10-3.

In this example, the diaphragm 6 is substantially disk-shaped as described above and is made of permalloy (an alloy of Ni—Fe) as the magnetic material. Hence the diaphragm 6 can be configured to be lighter than, for example, a rod-shaped movable iron core. In this instance, when the posture (direction) of the electronic valve 2 variously changes with respect to the vertical direction, the characteristic (e.g., the powering-current versus flow-rate characteristic) is hardly affected by the posture of the electronic valve 2.

As can be seen from FIGS. 2 and 3, a substantially cylindrical elastic body 8 for blocking the opening 4o is integrally attached to the center of the diaphragm 6 while facing the opening 4o formed in the recess 4d of the one end portion 4e of the pole piece 4. The elastic body 8 has a flat end face 8e projecting in a cylindrical shape from the diaphragm 6 toward the opening 4o of the one end portion 4e. In this example, the elastic body 8 is made of silicone rubber. However, the elastic body 8 may be made of other elastic materials (flexible material), such as nitrile rubber (NBR) and ethylene propylene diene rubber (EPDM). The outer diameter of the elastic body 8 is set larger than the diameter of the opening 4o and smaller than the inner diameter of the recess 4d. Thereby, in a closed state described later, the elastic body 8 having the flat end face 8e closes the opening 4o while being housed in a recess 4d having a flat bottom 4d1 opened toward the elastic body 8 at the one end portion 4e of the pole piece 4. Therefore, the elastic body 8 can stably and reliably close the opening 4o.

In this example, the elastic body 8 is integrally attached to the diaphragm 6 by insert molding. This enables easy and integral attachment of the elastic body 8 and the diaphragm 6. However, the present invention is not limited thereto, but the elastic body 8 may be attached to the diaphragm 6 by press-fitting, bonding, or the like.

Procedure for Assembling the Electronic Valve

The assembly of the electronic valve 2 is performed in the following procedure from the states illustrated in FIGS. 2 and 3 (disassembled state), for example.

i) First, the yoke 3 and the pole piece 4 are housed into the main case 10B. At this time, the projection 4a of the pole piece 4 is put and fitted into the through hole 10w of the first end wall 10-1 of the main case 10B. In addition, the through hole 3u of the end plate portion 3b of the yoke 3 is caused to correspond to the through hole 10u of the first end wall 10-1 of the main case 10B.

ii) Next, the solenoid coil 7 is housed into the annular space SP1 between the pole piece 4 and the side plate portion 3c of the yoke 3. At this time, a pair of lead wires (not illustrated) extending from the solenoid coil 7 are extracted to the outside of the main case 10B through the through hole 3u of the end plate portion 3b of the yoke 3 and the through hole 10u of the first end wall 10-1 of the main case 10B.

iii) Next, the pair of lead wires extracted are soldered one by one to any two of the four connection terminals 71, 72, 73, 74 provided on the outer surface of the first end wall 10-1. Note that the remaining two of the four connection terminals 71, 72, 73, 74 are left as dummy terminals.

iv) Next, the yoke 3 is bonded to the main case 10B, and the solenoid coil 7 is bonded to the yoke 3, both in an airtight manner using an adhesive. At this time, the air tightness is obtained by filling, with the adhesive, the through hole 3u of the end plate portion 3b of the yoke 3 and/or the through hole 10u of the first end wall 10-1 of the main case 10B, through which the pair of lead wires pass.

v) Next, the coil spring 5 is housed into the annular space SP2 (cf. FIG. 4) between the side plate portion 3c of the yoke 3 and the outer peripheral wall 10-3 of the main case 10B.

vi) Subsequently, the diaphragm 6 is disposed to face the end plate portion 3b of the yoke 3 from one side (+Z side) of the coil spring 5 through the space SP1. Further, while the diaphragm 6 is pressed against the biasing force f2 of the coil spring 5 with the lid case 10A, the second end wall 10-2 of the lid case 10A is welded to the outer peripheral wall 10-3 of the main case 10B in an airtight manner by an ultrasonic welding method.

In this manner, as illustrated in FIG. 4, the electronic valve 2 is assembled.

In the assembled state illustrated in FIG. 4, as the sealing case, the case 10 collectively covers, in an airtight manner, the yoke 3, the main portion 4b of the pole piece 4, the solenoid coil 7, the diaphragm 6 (and elastic body 8), and the coil spring 5 in a state that the projection 4a (it includes the other end portion 4f) of the pole piece 4 is exposed to the outside. While the first end wall 10-1 of the main case 10B is along the outer surface (the surface facing the −Z side) of the end plate portion 3b of the yoke 3, the second end wall 10-2 of the lid case 10A is along the rear surface (the surface facing +Z side) 6a of the diaphragm 6. In particular, in this example, the projection 4a of the pole piece 4 forming the first fluid inlet/outlet 11 projects to the outside from the first end wall 10-1, and the cylindrical portion 10a forming the second fluid inlet/outlet 12 projects to the outside from the second end wall 10-2. Therefore, the first fluid inlet/outlet 11 and the second fluid inlet/outlet 12 can be easily connected to, for example, a downstream side and an upstream side of the flow path so that fluid can flow therethrough. Hence the electronic valve 2 can be easily inserted into the flow path.

Opening/Closing Operation of Electronic Valve

Figure 6:
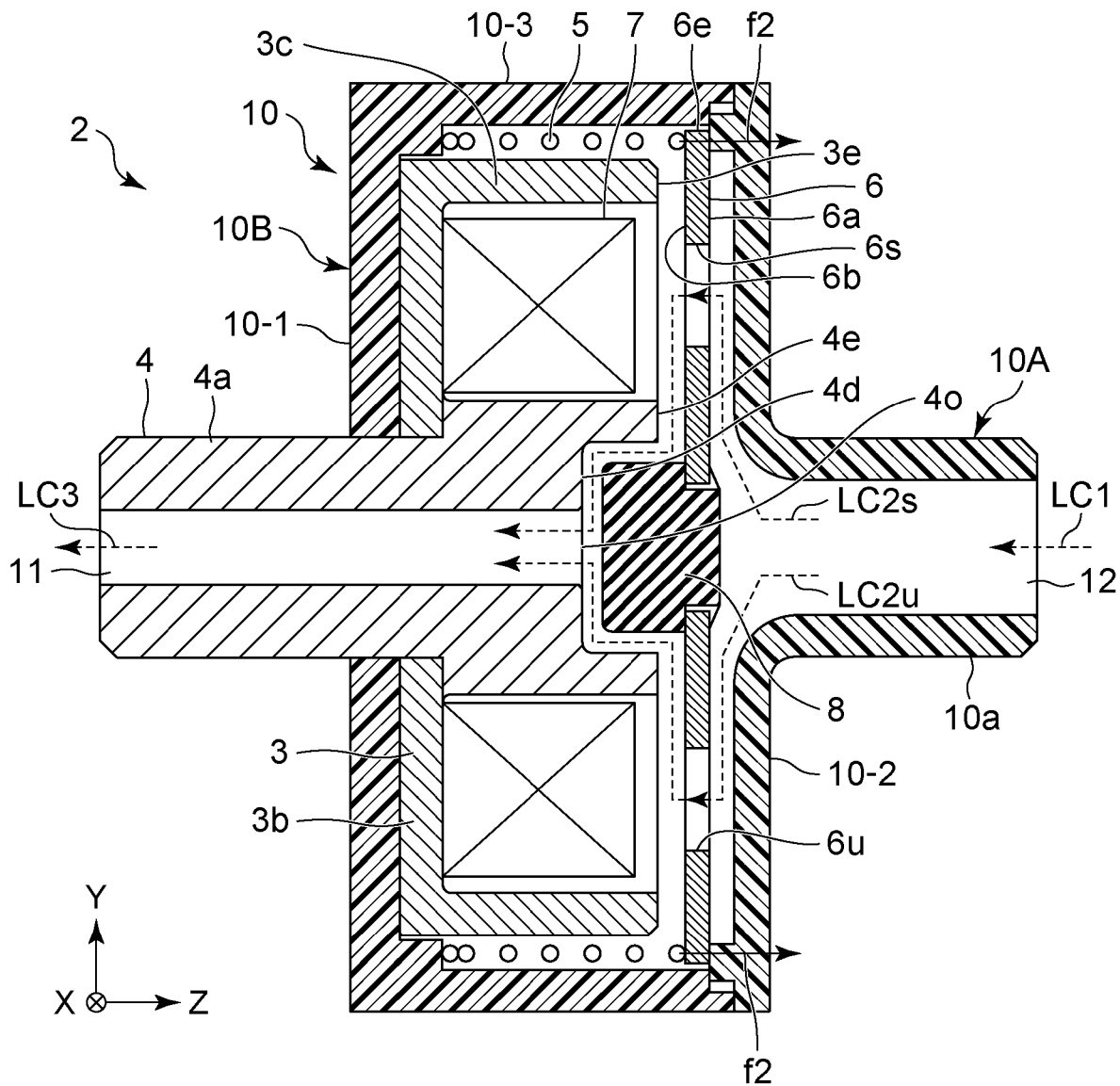
FIG. 6 illustrates a flow of fluid through the electronic valve when the electronic valve is in an open state.

When the electronic valve 2 is used, the electronic valve 2 is inserted into the flow path by connecting the first fluid inlet/outlet 11 and the second fluid inlet/outlet 12 to the downstream side and the upstream side of the flow path so that fluid can flow, respectively, as described above. As illustrated in FIG. 6, in the electronic valve 2, in the non-operating time when the solenoid coil 7 is in an unpowered state, the diaphragm 6 is separated from the one end portion 4e of the pole piece 4 by the biasing force f2 by the coil spring 5, whereby the end face 8e of the elastic body 8 is separated from the opening 4o of the one end portion 4e of the pole piece 4, and the electronic valve comes into an open state where the opening 4o is opened. That is, the electronic valve 2 is a normally-open valve.

In this open state, fluid is permitted to flow through the electronic valve 2. When the electronic valve 2 is in the open state, for example, the fluid enters from the second fluid inlet/outlet 12 as indicated by an arrow LC1. As indicated by arrows LC2s, LC2u, the fluid flows through the through holes 6s, 6t, 6u, 6v of the diaphragm 6, then passes through the gap between the recess 4d of the one end portion 4e of the pole piece 4 and the elastic body 8, passes through the opening 4o of the one end portion 4e, and flows from the first fluid inlet/outlet 11 to the outside as indicated by arrows LC3. As thus described, fluid can flow from the second fluid inlet/outlet 12 to the first fluid inlet/outlet 11, or in the opposite direction, through the electronic valve 2.

Figure 7:
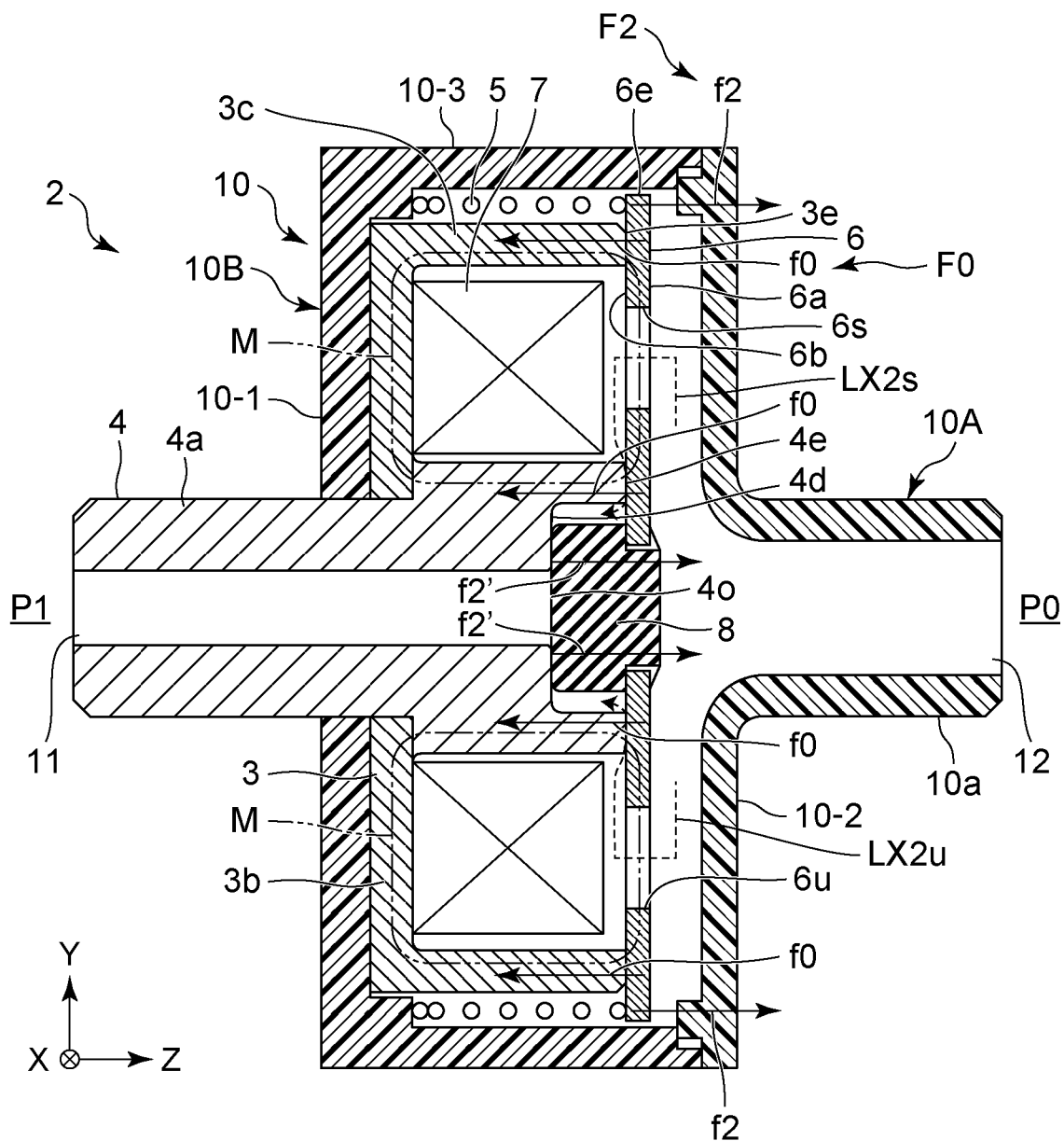
FIG. 7 illustrates a force applied to each portion of the electronic valve when the electronic valve is in a closed state.

In the operating time when the solenoid coil 7 is in a powered state, as illustrated in FIG. 7, the diaphragm 6 approaches the one end portion 4e of the pole piece 4 against the biasing force f2 by the coil spring 5 and a repulsive force f2' received by the elastic body 8 from the recess 4d of the one end portion 4e of the pole piece 4 (a resultant force of these f2 and f2' is expressed as a drag force F2) by a magnetic force F0 (a resultant force of magnetic forces f0, f0, . . . applied to the respective portions of the diaphragm 6) generated by the solenoid coil 7, whereby the electronic valve 2 comes into the closed state where the opening 4o of the one end portion 4e of the pole piece 4 is closed with the end face 8e of the elastic body 8. Specifically, when the solenoid coil 7 is in the powered state (in the operating time), as indicated by a two-dot chain lines M in FIG. 7, the magnetic lines of force generated by the solenoid coil 7 circulates a route (magnetic circuit) that mainly reaches the peripheral edge of the end plate portion 3b through the side plate portion 3c of the yoke 3, reaches the orthogonal position between the end plate portion 3b and the pole piece 4 through the end plate portion 3b from the peripheral edge of the end plate portion 3b, reaches the one end portion 4e of the pole piece 4 through the pole piece 4 from the orthogonal position, reaches the approach portion between the one end portion 4e and the diaphragm 6 from the one end portion 4e, and reaches the annular edge 3e of the side plate portion 3c of the yoke 3 through the diaphragm 6. When the powering direction to the solenoid coil 7 is reversed, the magnetic lines of force generated by the solenoid coil 7 circulates in the reverse direction in this route. Thus, the solenoid coil 7 generates the magnetic force F0 for the diaphragm 6 against the biasing force f2 by the coil spring 5. The diaphragm 6 approaches the one end portion 4e of the pole piece 4 by the magnetic force F0, and the electronic valve 2 comes into the closed state where the opening 4o is closed with the end face 8e of the elastic body 8. In the closed state, the flow of the fluid through the inside of the pole piece 4 is blocked. As thus described, the electronic valve 2 can come into the open state or the closed state depending on whether the solenoid coil 7 is in the unpowered state (non-operating time) or the solenoid coil 7 is in the powered state (in the operating time). Thereby, the flow of the fluid in the pole piece 4, that is, the flow of the fluid through the electronic valve 2, can be permitted or blocked.

In the closed state illustrated in FIG. 7, the inner surface 6b of the diaphragm 6 comes into contact with a peripheral end face 4e1 of the one end portion 4e of the pole piece 4. However, as indicated by arrows LX2s, LX2u, the fluid can pass through the through holes 6s, 6t, 6u, 6v of the diaphragm 6, pass between the inner surface 6b of the diaphragm 6 and the peripheral end face 4e1, and enter the gap between the recess 4d of the one end portion 4e of the pole piece 4 and the elastic body 8. Hence the influence of the pressure (rear-side pressure) P0 of the fluid applied to the rear surface 6a of the diaphragm 6 on the powering-current (or drive-voltage) versus flow-rate characteristic has been reduced.

Figure 10:
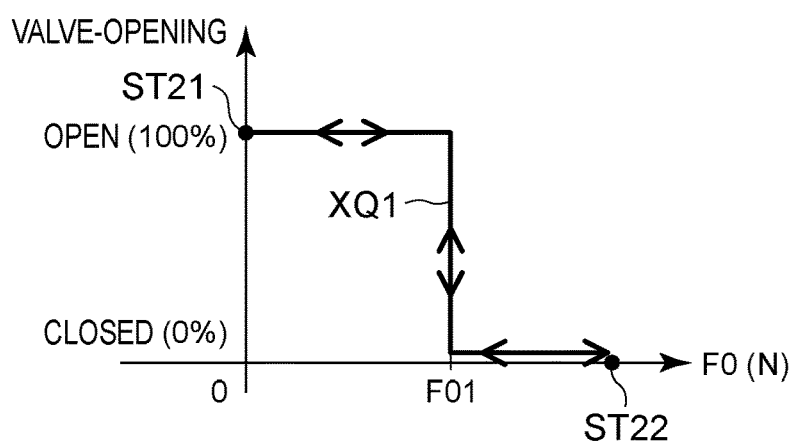
FIG. 10 is a diagram illustrating a relationship between a driving force and a valve-opening of the electronic valve.

For example, FIG. 10 illustrates the relationship between the magnetic force F0 generated by the solenoid coil 7 and the valve-opening of the electronic valve 2. The valve-opening is 100% when the valve is fully open and 0% when the valve is fully closed. For simplicity, a description will be given disregarding the intermediate state between the open state and the closed state of each valve.

It is assumed that the electronic valve 2 is initially at a point ST21 where the magnetic force F0=0, and thus the valve-opening is 100%. When the powered amount of the solenoid coil 7 is increased to increase the magnetic force F0, as illustrated by a solid line XQ1, in this example, the state shifts from the open state to the closed state when the magnetic force F01 is applied. In this example, the magnetic force F0 is temporarily stopped at a point ST22 at which the magnetic force F0 slightly exceeds F01. Here, in the electronic valve 2, when the powered amount of the solenoid coil 7 is reduced to reduce the magnetic force F0, the electronic valve 2 is reversed on the solid line XQ1, and returns to the open state when approximately the magnetic force F01 is applied. Then, the electronic valve 2 returns to the first point ST21.

For example, the drag force due to the coil spring 5 or the like is assumed to be F2=5.0×10$^{-2}$ [N]. Then, under conditions of rear-side pressure P0=0 mmHg and opening-side pressure (the pressure of the fluid applied to the opening 4o from the first fluid inlet/outlet 11 side) P1=0 mmHg, the magnetic force at the time of shifting from the open state to the closed state along the arrow XQ1 in FIG. 10 (or, conversely, at the time of shifting from the closed state to the open state) becomes F01≈F2=5.0×10$^{-2}$ [N]. Also, under conditions of the rear-side pressure P0=300 mmHg and the opening-side pressure P1=300 mmHg, F01≈F2=5.0×10$^{-2}$ [N] is satisfied in the same manner. Note that the diameter of the opening 4o is set to Φ=0.5 mm, and the diameter of the recess 4d at the one end portion 4e of the pole piece 4 is set to Φa =1.2 mm. Then, for example, under conditions of the rear-side pressure P0=0 mmHg and the opening-side pressure P1=300 mmHg, a pressing force (assumed to be F1) to the diaphragm 6 due to the opening-side pressure P1 becomes F1=7.84×10$^{-3}$ [N] because the area (assumed to be S0) of the opening 4o is S0=πΦ$^2$/4. Therefore, F01≈F1+F2=5.8×10$^{-2}$ [N].

As the open/closed state of the electronic valve 2, the intermediate state exists between the closed state and the open state in which the flow rate is controlled in accordance with the powered amount of the solenoid. When the state shifts from the open state to the closed state, the elastic body 8 of the diaphragm 6 approaches the opening 4o at the one end portion 4e of the pole piece 4. Thereby, a stable powering-current (or drive-voltage) versus flow-rate characteristic can be obtained.

In this electronic valve 2, in order to permit or block the flow of fluid, the plate-shaped diaphragm 6 is configured to move translationally in one direction (Z direction) approaching or separating from the one end portion 4e of the pole piece 4 in a posture facing the end plate portion 3b of the yoke 3. That is, unlike the conventional example (the movable iron core has a rod shape and moves along its longitudinal direction), in this electronic valve 2, the plate-shaped diaphragm 6 moves in one direction (Z direction) perpendicular to the plate surface of the diaphragm 6. Therefore, the size of the electronic valve 2 can be reduced with respect to one direction (Z direction) in which the diaphragm 6 moves. As a result, the electronic valve 2 can be formed in small size.

Particularly, in the electronic valve 2, by setting the size of the case 10 from the first end wall 10-1 to the second end wall 10-2 to be small, it is possible to have a flattend outer shape along the first and second end walls 10-1, 10-2. Such an outer shape is suitable for mounting the electronic valve 2 (case 10) along, for example, a wiring board, to form the electronic valve 2 (case 10) and the wiring board to be totally flattend.

In this example, as illustrated in FIG. 1, a thickness (dimension in the z direction) H of the case 10 is set to about 2.5 mm. Dimensions W1, W2 (dimensions in the XY direction) of the case 10 in the plane direction are set to about 5.5 mm, respectively. In this way, the case 10 has a flattend outer shape. In this example, the dimension of the cylindrical portion 10a of the lid case 10A projecting from the second end wall 10-2 to the +Z side is set to about 1.6 mm. The outer diameter and the inner diameter of the cylindrical portion 10a are set to about 1.3 mm and about 0.8 mm, respectively. The dimension of the projection 4a of the pole piece 4 projecting from the first end wall 10-1 of the main case 10B to the −Z side is set to about 1.6 mm. The outer diameter and the inner diameter of the projection 4a of the pole piece 4 are set to about 1.3 mm and about 0.5 mm, respectively. As thus described, the electronic valve 2 can be formed in small size.

The electronic valve 2 can be reduced in weight as a result that the electronic valve 2 can be formed in small size. In particular, the electronic valve 2 is provided with the plate-shaped diaphragm 6 made of permalloy in place of the rod-shaped movable iron core of the conventional electronic valve, so that the electronic valve 2 can be reduced in weight. Further, even when the posture of the electronic valve 2 variously changes with respect to the vertical direction, the change in the characteristic (e.g., powering-current (or drive-voltage) versus flow-rate characteristic) is small. It is thus possible to stably and reliably open and close the electronic valve 2.

Application to Sphygmomanometer

Figure 8:
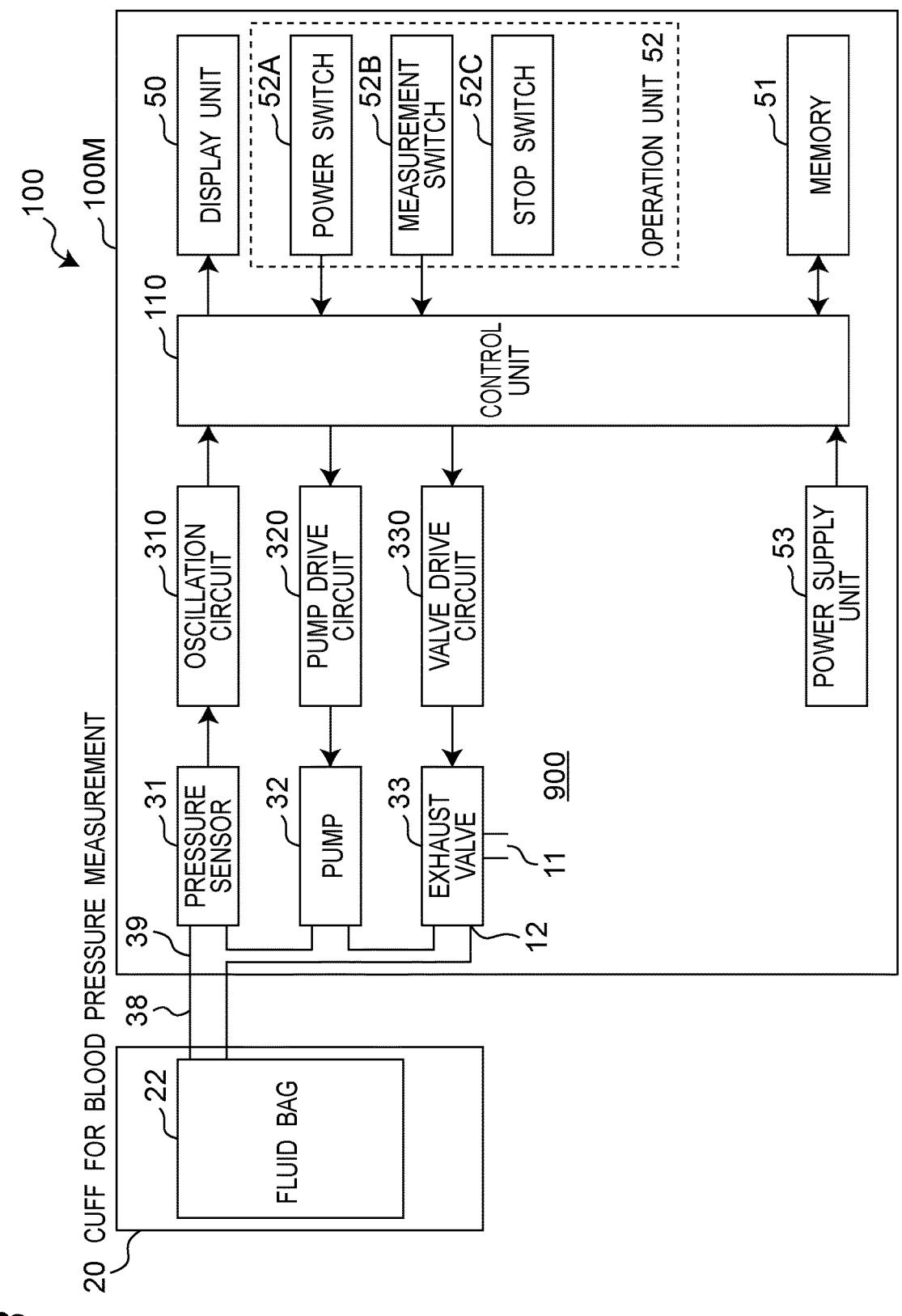
FIG. 8 is a diagram illustrating a block configuration of a sphygmomanometer according to an embodiment of the present invention, which includes the electronic valve as an on-off valve.

FIG. 8 illustrates a schematic block configuration of an electronic sphygmomanometer (the whole is denoted by reference numeral 100) according to an embodiment of the present invention. The sphygmomanometer 100 is roughly provided with a cuff 20 to be attached to a part to be measured, such as a wrist or an upper arm, and a body 100M.

The cuff 20 includes a fluid bag 22 for compressing the part to be measured. The fluid bag 22 and the main body 100M are connected to each other so as to permit fluid to flow through an air tube 38 having flexibility.

The main body 100M includes a control unit 110, a display unit 50, a memory 51 serving as a storage unit, an operation unit 52, a power supply unit 53, a pressure sensor 31, a pump 32, and an exhaust valve 33 made of the electronic valve 2 described above. The main body 100M further includes an oscillation circuit 310 for converting an output from the pressure sensor 31 into a frequency, a pump drive circuit 320 for driving the pump 32, and a valve drive circuit 330 for driving the exhaust valve 33. The pressure sensor 31, the pump 32, and the exhaust valve 33 are connected to the air tube 38 through a common air pipe 39 provided in the main body 100M so as to permit fluid to flow. In this example, in the exhaust valve 33, the second fluid inlet/outlet 12 is connected in communication with the air pipe 39, and the first fluid inlet/outlet 11 is opened toward the atmosphere 900.

The display unit 50 includes a display, an indicator, and the like, and displays predetermined information (e.g., blood pressure measurement results) in accordance with a control signal from the control unit 110.

The operation unit 52 includes a power switch 52A for receiving an instruction input to turn on or turn off the power supply unit 53, a measurement switch 52B for receiving an instruction to start measurement of blood pressure, and a stop switch 52C for receiving an instruction to stop measurement. These switches 52A, 52B, 52C input operation signals in accordance with instructions from a user to the control unit 110.

The memory 51 stores data of a program for controlling the sphygmomanometer 100, data to be used for controlling the sphygmomanometer 100, setting data for setting various functions of the sphygmomanometer 100, data of measurement results of blood pressure values, and the like. The memory 51 is used as a work memory at the time of executing a program, and the like.

The control unit 110 includes a central processing unit (CPU) and controls the entire operation of the sphygmomanometer 100. Specifically, the control unit 110 functions as a pressure control unit in accordance with the program for controlling the sphygmomanometer 100 which is stored in the memory 51, and performs control for driving the pump 32 and the exhaust valve 33 in accordance with an operation signal from the operation unit 52. The control unit 110 functions as a blood pressure calculation unit to calculate a blood pressure value and controls the display unit 50 and the memory 51. A specific method for measuring blood pressure will be described later.

The power supply unit 53 supplies electric power to each of the control unit 110, the pressure sensor 31, the pump 32, the exhaust valve 33, the display unit 50, the memory 51, the oscillation circuit 310, the pump drive circuit 320, and the valve drive circuit 330.

The pump 32 supplies air as the fluid to the fluid bag 22 to pressurize the pressure (cuff pressure) in the fluid bag 22 contained in the cuff 20. The exhaust valve 33 is opened to discharge the air from the fluid bag 22 or closed to enclose the air inside the fluid bag 22 to control the cuff pressure. The pump drive circuit 320 drives the pump 32 based on a control signal given from a control unit 110. The valve drive circuit 330 opens or closes the exhaust valve 33 based on a control signal supplied from the control unit 110.

The pressure sensor 31 and the oscillation circuit 310 function as a pressure detection unit that detects the pressure of the cuff. The pressure sensor 31 is, for example, a piezoresistive pressure sensor, and detects the pressure (cuff pressure) in the fluid bag 22 contained in the cuff 20 through the air pipe 39 and the air tube 38. In this example, the oscillation circuit 310 oscillates in accordance with an electrical signal value based on a change in electrical resistance due to a piezoresistive effect from the pressure sensor 31, and outputs a frequency signal having a frequency corresponding to the electrical signal value of the pressure sensor 31 to the control unit 110.

Figure 9A:
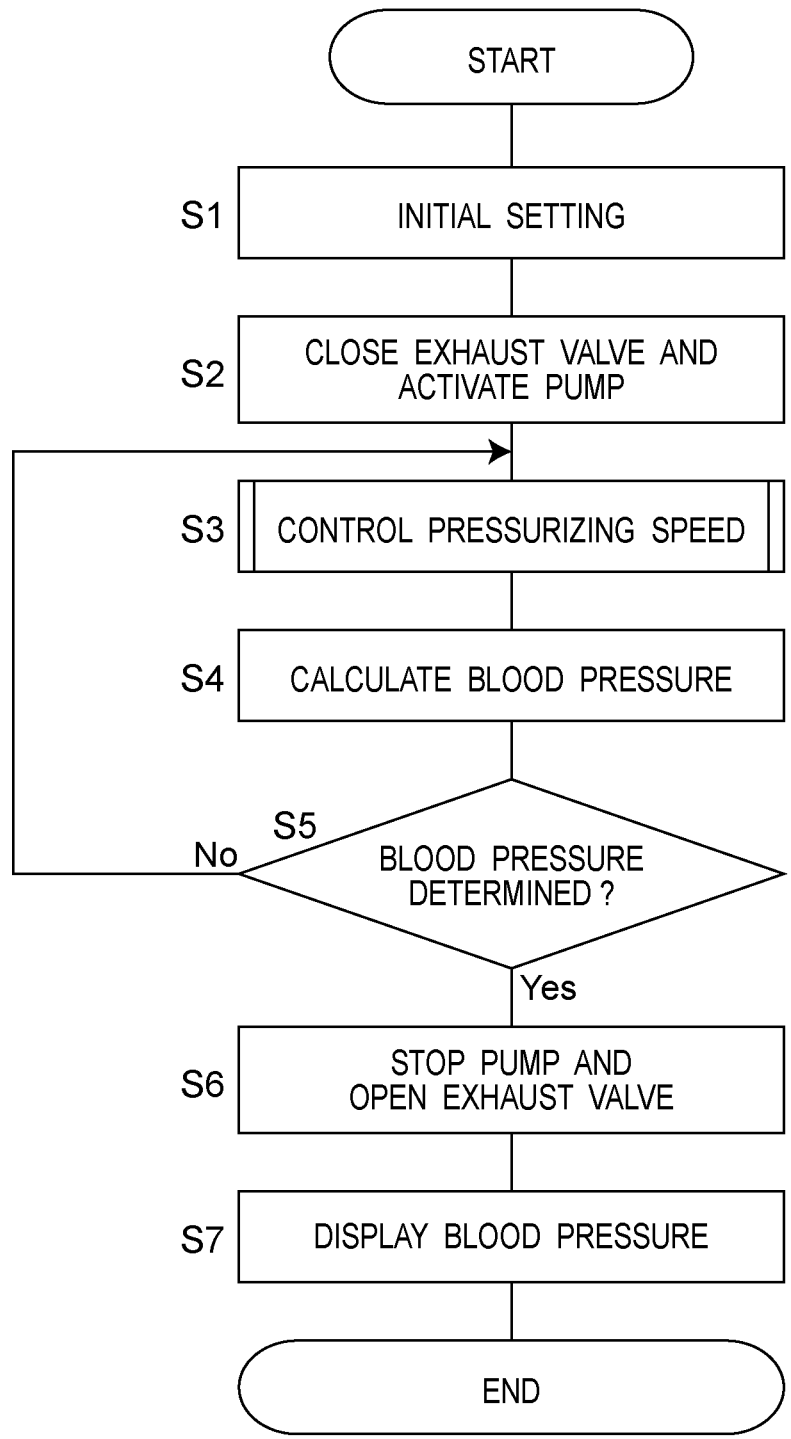
FIG. 9A is a diagram illustrating an operation flow of the sphygmomanometer.

FIG. 9A illustrates an operation flow when the user performs blood pressure measurement with the sphygmomanometer 100.

When the user instructs the start of the measurement by using the operation unit 52 provided in the main body 100M with the cuff 20 attached to the part to be measured, the control unit 110 performs initial setting (step S1 of FIG. 9A). Specifically, the control unit 110 initializes the processing memory area, turns off (stops) the pump 32, and adjusts the pressure sensor 31 to 0 mmHg (set the atmospheric pressure to 0 mmHg.) with the exhaust valve 33 open.

Next, the control unit 110 closes the exhaust valve 33 via the valve drive circuit 330 and then turns on (activates) the pump 32 via the pump drive circuit 320 to start pressurizing the cuff 20 (fluid bag 22) (step S2). The control unit 110 controls the pressurizing speed based on the output of the pressure sensor 31 while supplying air from the pump 32 to the fluid bag 22 through the air pipe 39 and the air tube 38 (step S3).

Figure 9B:
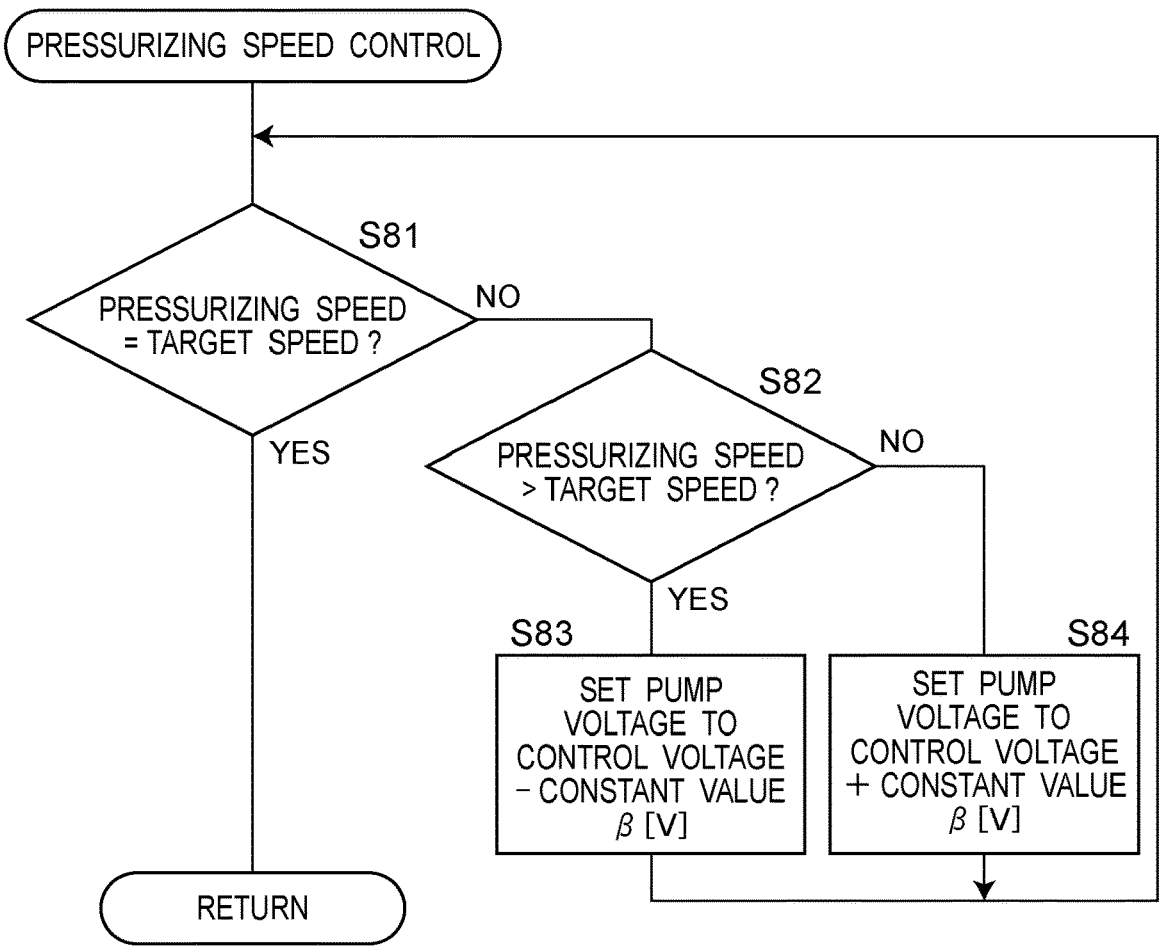
FIG. 9B is a diagram illustrating a flow of pressurizing speed control included in the operation flow of FIG. 9A.

Specifically, in this example, as illustrated in the flow of the pressurizing speed control in FIG. 9B, the control unit 110 determines whether or not the pressurizing speed matches a target speed (step S81 of FIG. 9B). When the pressurizing speed matches the target speed (YES in step S81), the process returns to the flow of FIG. 9A. On the other hand, when the pressurizing speed does not match the target speed (NO in step S81 of FIG. 9B), the process proceeds to step S82 in FIG. 9B, where it is determined whether or not the pressurizing speed is larger than the target speed. When the pressurizing speed is larger than the target speed (YES in step S82), the drive-voltage of the pump 32 is decreased from a current control voltage by a constant value β [V] (step S83). On the other hand, when the pressurizing speed is smaller than the target speed (NO in step S82), the drive-voltage of the pump 32 is increased from the current control voltage by a constant value β [V] (step S84). Thereafter, the flow returns to the flow of FIG. 9A.

Next, in step S4 in FIG. 9A, the control unit 110 functions as a blood pressure calculation unit and tries to calculate a blood pressure value (systolic blood pressure (SBP) and diastolic blood pressure (DBP)) by a known oscillometric method based on a pulse wave signal (fluctuation components due to pulse waves included in the output of the pressure sensor 31) acquired at this point in time.

At this point in time, when the blood pressure value cannot be calculated due to the lack of data (NO in step S5), the processing of steps S3 to S5 is repeated unless the cuff pressure has reached the upper limit pressure (predetermined for safety, it is predetermined, for example, 300 mmHg.).

After the blood pressure value is calculated in this manner (YES in step S5), the control unit 110 displays the measurement result of the blood pressure value on the display unit 50. Further, the control unit 110 performs control to turn off the pump 32, opens the exhaust valve 33 (step S6), and exhausts the air in the cuff 20 (fluid bag 22).

Thereafter, the control unit 110 displays the calculated blood pressure value on the display unit 50 (step S7) and controls to store the blood pressure value in the memory 51.

Note that the blood pressure calculation may be performed in a depressurization process rather than the pressurization process over the cuff 20 (fluid bag 22).

In the sphygmomanometer 100, the exhaust valve 33 is made of an electronic valve 2 that is formed in small size and in light weight. Thus, not only the main body 100M but also the whole of the sphygmomanometer 100 can be formed in small size and in light weight. Further, even when the posture of the exhaust valve 33 (electronic valve 2) variously changes with respect to the vertical direction, the change in characteristic (e.g., powering-current (or drive-voltage) versus flow-rate characteristic) is small. Accordingly, it is possible to stably and reliably open and close the exhaust valve 33, and to thereby stabilize the operation of the sphygmomanometer 100.

Modifications Related to the Case

In the above example, the second fluid inlet/outlet 12 of the electronic valve 2 has been made of the cylindrical portion 10a projecting to the outside (+Z side) from the second end wall 10-2 of the lid case 10A. In this instance, it becomes easy to insert the electronic valve 2 into the straight flow path. However, the present invention is not limited thereto.

Figure 11A:
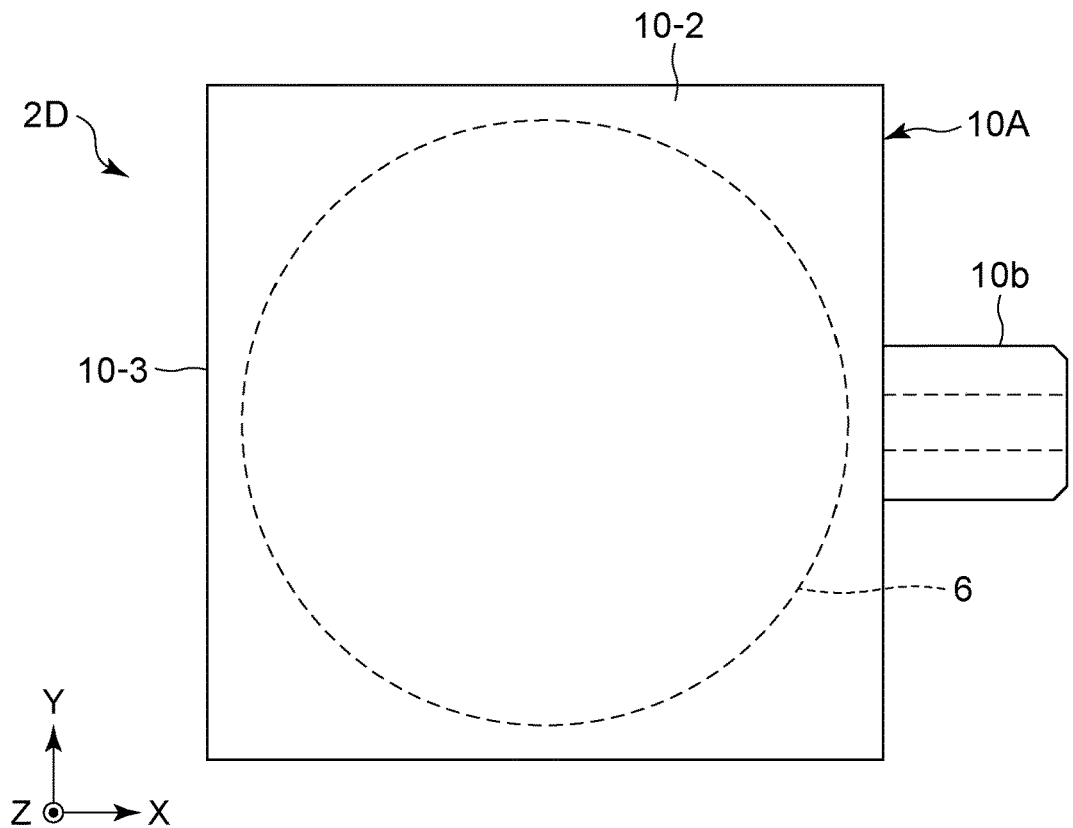
FIGS. 11A and 11B are views illustrating an example of an electronic valve formed by modifying the case of the electronic valve.
Figure 11B:
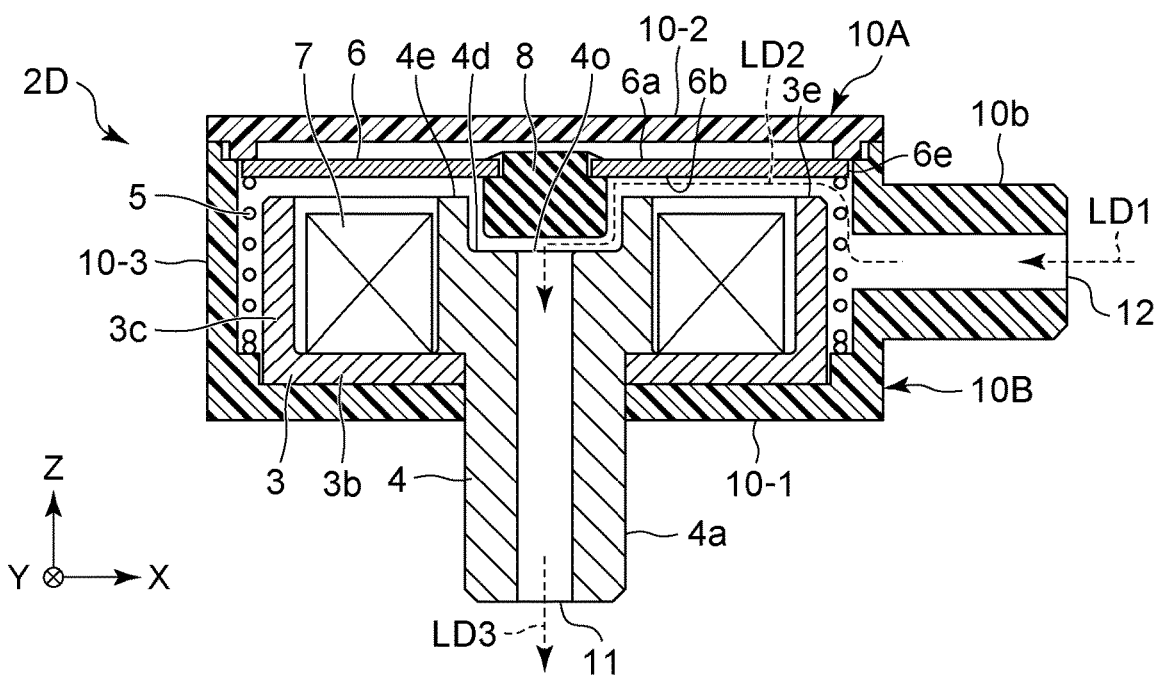

For example, FIGS. 11A and 11B illustrate an example of an electronic valve 2D obtained by modifying the case 10 of the electronic valve 2. FIG. 11A illustrates the electronic valve 2D viewed from the +Z side. FIG. 11B illustrates a cross-sectional structure viewed from the lower side (−Y side) in FIG. 11A. As can be seen from this figure, in the electronic valve 2D, a cylindrical portion 10b forming the second fluid inlet/outlet 12 is disposed projecting to the outside (+X side) from the outer peripheral wall 10-3 of the main case 10B. In the other respects, the electronic valve 2D is configured in the same manner as in the electronic valve 2 (In FIG. 11B, for simplicity, the structure of the diaphragm 6 is illustrated in a simplified manner as compared to FIGS. 4, 6 and 7. This also applies to FIG. 12B to be described later.).

When the electronic valve 2D is in the open state, fluid enters from the second fluid inlet/outlet 12 as indicated by an arrow LD1 in FIG. 11B. As indicated by an arrow LD2, the fluid passes through the gap between the inner surface 6b of the diaphragm 6 and the annular edge 3e of the side plate portion 3c of the yoke 3, the gap between the inner surface 6b of the diaphragm 6 and the one end portion 4e of the pole piece 4, and the gap between the recess 4d of the one end 4e of the pole piece 4 and the elastic body 8 in order, and flows from the first fluid inlet/outlet 11 to the outside through the opening 4o of the one end portion 4e as indicated by an arrow LD3. In this way, the fluid can flow from the second fluid inlet/outlet 12 to the first fluid inlet/outlet 11, or in the opposite direction, through the electronic valve 2D.

When the electronic valve 2D is in the closed state, as in the electronic valve 2, the diaphragm 6 approaches to the one end portion 4e of the pole piece 4, and the opening 4o is closed with the elastic body 8.

In this electronic valve 2D, it is possible to prevent the cylindrical portion 10b forming the second fluid inlet/outlet 12 from projecting to the outside (+Z side) from the second end wall 10-2 of the lid case 10A. As a result, the electronic valve can be formed in thin size. For example, the main case 10B is attached along the upper surface of the wiring board (not illustrated), the projection 4a forming the first fluid inlet/outlet 11 is extended downward through the wiring board, so that the electronic valve 2D and the wiring board can be formed totally flattend.

Figure 12A:
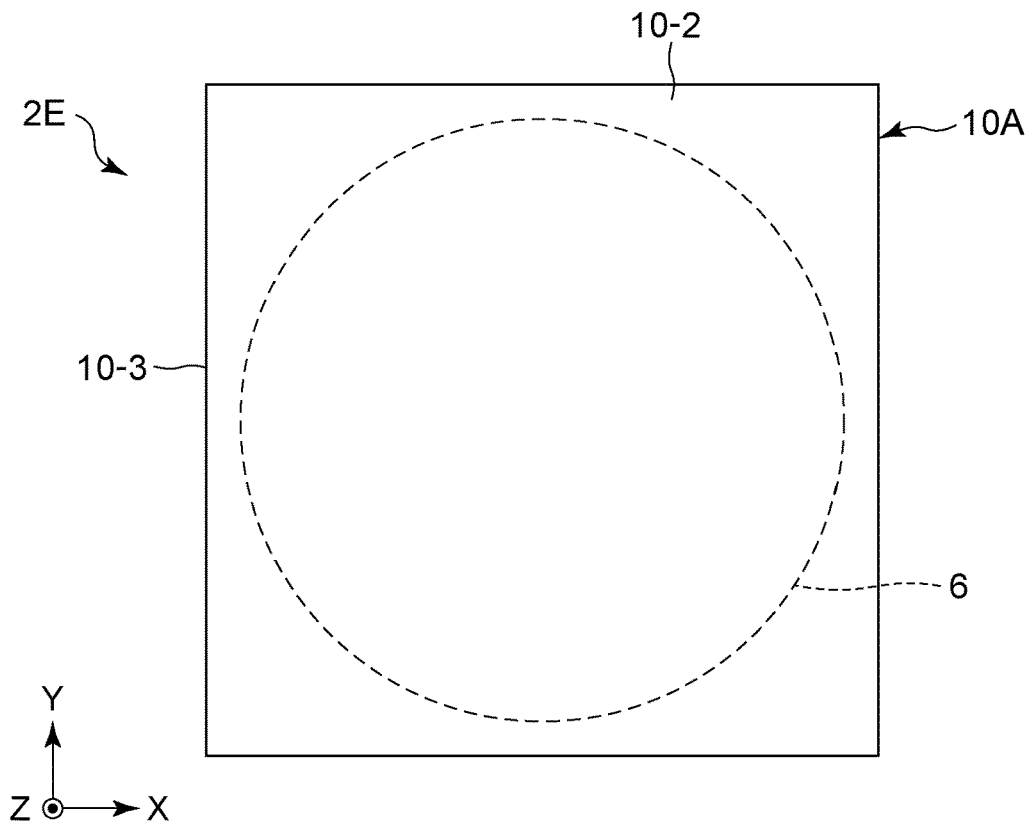
FIGS. 12A and 12B are views illustrating another example of the electronic valve formed by modifying the case of the electronic valve.
Figure 12B:
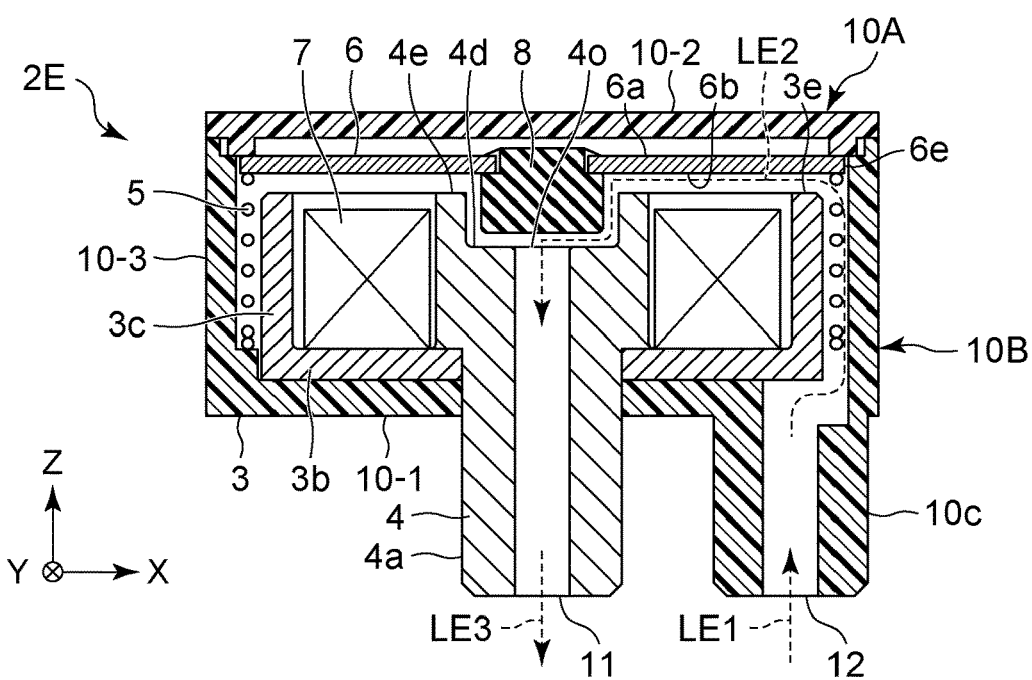

FIGS. 12A and 12B illustrate another example of an electronic valve 2E formed by modifying the case 10 of the electronic valve 2. FIG. 12A illustrates the electronic valve 2E viewed from the +Z side. FIG. 12B illustrates a cross-sectional structure viewed from the lower side (−Y side) in FIG. 12A. As can be seen from this figure, in the electronic valve 2E, a cylindrical portion 10c forming the second fluid inlet/outlet 12 is disposed projecting to the outside (−Z side) from the first end wall 10-1 of the main case 10B. In the other respects, the electronic valve 2E is configured in the same manner as in the electronic valve 2.

When the electronic valve 2E is in the open state, fluid enters from the second fluid inlet/outlet 12 into FIG. 12B as indicated by an arrow LE1. As indicated by an arrow LE2, the fluid passes through the gap between the outer peripheral wall 10-3 of the main case 10B and the side plate portion 3c of the yoke 3, the gap between the inner surface 6b of the diaphragm 6 and the annular edge 3e of the side plate portion 3c of the yoke 3, the gap between the inner surface 6b of the diaphragm 6 and the one end portion 4e of the pole piece 4, and the gap between the recess 4d of the one end portion 4e of the pole piece 4 and the elastic body 8 in order, and flows from the first fluid inlet/outlet 11 to the outside through the opening 4o of the one end portion 4e as indicated by an arrow LE3. In this way, the fluid can flow from the second fluid inlet/outlet 12 to the first fluid inlet/outlet 11, or in the opposite direction, through the electronic valve 2E.

When the electronic valve 2E is in the closed state, as in the electronic valve 2, the diaphragm 6 approaches to the one end portion 4e of the pole piece 4, and the opening 4o is closed with the elastic body 8.

In this electronic valve 2E, similarly to the electronic valve 2D, it is possible to prevent the cylindrical portion 10c forming the second fluid inlet/outlet 12 from projecting to the outside (+Z side) from the second end wall 10-2 of the lid case 10A. As a result, the electronic valve can be formed in thin size. Further, in the electronic valve 2E, the cylindrical portion 10c forming the second fluid inlet/outlet 12 can be projected in the same direction (−Z direction) as the projection 4a forming the first fluid inlet/outlet 11. For example, the main case 10B is attached along the upper surface of the wiring board (not illustrated), the cylindrical portion 10c and the projection 4a are both extended downward through the wiring board, so that the electronic valve 2E and the wiring board can be formed totally flattend. In this instance, a flow path connected to the electronic valve 2E can be disposed only below the wiring board.

Application to Apparatus

In the above embodiment, the electronic valve of the present invention has been applied to the sphygmomanometer, but the present invention is not limited thereto. The electronic valve of the present invention can be applied to various apparatuses other than the sphygmomanometer. The electronic valve of the present invention can also be applied to an apparatus including functional units for performing a blood pressure measuring function and various other functions. In this instance, the apparatus can be formed in small size and in light weight. Even when the posture of the electronic valve variously changes with respect to the vertical direction, the change in characteristic (e.g., powering-current versus flow-rate characteristic) is small, whereby it is possible to stably and reliably open and close the electronic valve and to stabilize the operation of the apparatus.

In order to achieve the above object, an electronic valve according to the present disclosure is an electronic valve that permits or blocks a flow of fluid, the electronic valve comprising:

a yoke including an end plate portion having an annular peripheral edge, and a side plate portion connected to the peripheral edge of the end plate portion and annularly surrounding a space adjacent to one side of the end plate portion;

a pole piece orthogonal to the end plate portion of the yoke and extending in one direction from one end portion existing in the space of the one side to other end portion of opposite side, the pole piece having an opening at the one end portion and having, at the other end portion, a first fluid inlet/outlet in communication with the opening through an inside of the pole piece;

a solenoid coil housed in an annular space between the pole piece and the side plate portion of the yoke;

a diaphragm made of a disk-shaped magnetic material that faces the end plate portion of the yoke via the space and has a dimension extending over the annular edge of the side plate portion of the yoke;

a coil spring that biases the diaphragm in a direction away from the one end portion of the pole piece in a manner of moving the diaphragm translationally in the one direction; and a casing that collectively covers the yoke, a portion of the pole piece extending into the space of the one side, the solenoid coil, the diaphragm, and the coil spring, with the other end portion of the pole piece exposed to an outside, wherein the coil spring is disposed along an annular space between the side plate portion of the yoke and an annular outer peripheral wall of the casing facing the side plate portion, and is in annular contact with a peripheral edge portion of a surface of the diaphragm facing the end plate portion, a gap in a radial direction is provided between the annular outer peripheral wall of the casing and the peripheral edge portion of the diaphragm, an elastic body for closing the opening is integrally attached to a portion of the diaphragm facing the opening at the one end portion of the pole piece, and the elastic body has a flat end face projecting in a columnar shape from the diaphragm toward the opening at the one end, the pole piece has, at the one end portion, a recess having a flat bottom opened toward the elastic body attached to the diaphragm, and the opening is opened at the bottom of the recess, in a non-operating time when the solenoid coil is in an unpowered state, the diaphragm is separated from the one end portion of the pole piece by a biasing force of the coil spring, causing the end face of the elastic body being separated from the opening, such that the electronic valve comes into an open state where the opening is opened, and in an operating time when the solenoid coil is in a powered state, the diaphragm approaches the one end portion of the pole piece against the biasing force of the coil spring by a magnetic force generated by the solenoid coil, such that the electronic valve is able to come into a closed state where the opening is closed with the end face of the elastic body.

In the present specification, a "yoke" and a "pole piece" are elements each serving to guide magnetic lines of force as is known in the field of electromagnets, and are each made of a magnetic material (in particular, ferromagnetic materials such as iron are preferred.).

The peripheral edge of the end plate portion of the yoke widely includes an annular shape such as a circular shape or a round square (rounded square) shape. This also applies to the annular shape of the side plate portion of the yoke.

The "annular edge" of the side plate portion of the yoke refers to the edge on the opposite side to the end plate portion.

The "other end" of the pole piece may project from the end plate portion of the yoke or may stop on an outer surface of the end plate portion (the surface facing the opposite side to the space of the one side out of the two surfaces of the end plate portion).

In the present specification, the "elastic body" refers to an object made of an elastic material (flexible material), such as silicone rubber, nitrile rubber (NBR), or ethylene propylene diene rubber (EPDM).

As an open/closed state of the valve, an intermediate state exists between the closed state and the open state in which a flow rate is controlled in accordance with the powered amount of the solenoid.

In the disclosed electronic valve, in the non-operating time when the solenoid coil is in the unpowered state, the diaphragm is separated from the one end of the pole piece by the biasing force of the coil spring, causing the end face of the elastic body being separated from the opening, such that the electronic valve comes into an open state where the opening is opened. In the open state, the fluid is permitted to flow through the inside of the pole piece. This electronic valve is a normally-open valve.

In the operating time when the solenoid coil is in the powered state, the diaphragm approaches the one end of the pole piece against the biasing force of the coil spring by a magnetic force generated by the solenoid coil, such that the electronic valve can come into a closed state where the opening is closed with the end face of the elastic body. Specifically, when the solenoid coil is in the powered state (in the operating time), magnetic lines of force generated by the solenoid coil circulates a route (magnetic circuit) that, for example, reaches the peripheral edge of the end plate portion of the yoke through the side plate portion, reaches an orthogonal position between the end plate portion and the pole piece from the peripheral edge of the end plate portion through the end plate portion, reaches the one end portion of the pole piece through the pole piece from the orthogonal position, reaches an approach portion between the one end portion and the diaphragm from the one end portion, and reaches the annular edge of the side plate portion of the yoke through the diaphragm. When the direction of power to the solenoid coil is reversed, the magnetic lines of force generated by the solenoid coil circulates in the reverse direction in this route. Thus, the solenoid coil generates a magnetic force for the diaphragm against the biasing force of the coil spring. By this magnetic force, the elastic body attached to the diaphragm approaches the one end portion of the pole piece (thereby, a stable powering-current (or drive-voltage) versus flow-rate characteristic can be obtained), and the opening can come into the closed state with the end face of the elastic body. In the closed state, the flow of the fluid through the inside of the pole piece is blocked. As thus described, the electronic valve can come into the open state or the closed state depending on whether the solenoid coil is in the unpowered state (non-operating time) or the solenoid coil is in the powered state (in the operating time). It is thereby possible to permit or block the flow of the fluid through the pole piece (i.e., the electronic valve). In particular, in the closed state, the elastic body having the flat end face projecting from the diaphragm in a columnar shape closes the opening in the state of being housed in the recess having a flat bottom opened toward the elastic body at the one end portion of the pole piece. Therefore, the elastic body can stably and reliably close the opening.

In this electronic valve, in order to permit or block the flow of fluid, a plate-shaped diaphragm is configured to move translationally in one direction approaching or separating from the one end portion of the pole piece in a posture facing the end plate portion of the yoke. That is, unlike the conventional example (the movable iron core has a rod shape and moves along its longitudinal direction), in this electronic valve, the plate-shaped diaphragm moves in one direction perpendicular to the plate surface of the diaphragm. Therefore, the size of the electronic valve can be reduced with respect to the one direction in which the diaphragm moves. As a result, the electronic valve can be formed in small size.

Note that the elastic body is preferably attached to the diaphragm by press-fitting, bonding, or insert molding. This enables easy and integral attachment of the elastic body to the diaphragm.

In the electronic valve according to one embodiment, the pole piece and the yoke are configured integrally.

In the electronic valve of this one embodiment, with the pole piece and the yoke being configured integrally, the magnetic resistance between the pole piece and the yoke is small, and the efficiency of a magnetic circuit passing through the pole piece and the yoke is enhanced. Air leakage can be prevented by improving airtightness between the pole piece and the yoke.

In the electronic valve according to one embodiment, a magnetic material forming the diaphragm is permalloy.

Here, "permalloy" refers to an alloy of Ni—Fe.

In the electronic valve of this one embodiment, since the diaphragm is plate-shaped and made of permalloy, the diaphragm can be configured to be lighter than, for example, a rod-shaped movable iron core. In this instance, when the posture (direction) of the electronic valve variously changes with respect to the vertical direction, the characteristic (e.g., the powering-current versus flow-rate characteristic) is hardly affected by the posture of the electronic valve.

If the element that is driven to open and close the valve is a rod-shaped movable iron core, which has a relatively large weight, when the posture (direction) of the electronic valve variously changes with respect to the vertical direction, a gravity component that the movable iron core receives along the sliding direction changes substantially, to greatly affect the characteristic of the electronic valve.

In the electronic valve according to one embodiment, the casing is a sealing case that collectively covers, in a fluid-tight manner, the yoke, a portion of the pole piece extending into the space of the one side, the solenoid coil, the diaphragm, and the coil spring, with the other end portion of the pole piece exposed to an outside; and a second fluid inlet/outlet provided through an outer wall of the sealing case.

The electronic valve of the present embodiment is suitable for being interposed in the flow path to permit or block the flow of fluid through the flow path. When the electronic valve is in the open state, for example, fluid can flow from the second fluid inlet/outlet to the first fluid inlet/outlet through the opening (being in the open state with the diaphragm separated from the one end portion) at the one end portion of the pole piece, or in the opposite direction, through the electronic valve. When the electronic valve is in the closed state, since the opening (being in the closed state with the diaphragm approaching the one end portion) has been blocked, no fluid flows between the second fluid inlet/outlet and the first fluid inlet/outlet through the electronic valve.

In the electronic valve according to one embodiment,
the sealing case includes
a first end wall along an outer surface of the end plate portion of the yoke,
a second end wall along a rear surface of the diaphragm facing an opposite side to the end plate portion, and
the annular outer peripheral wall connecting a peripheral edge portion of the first end wall and a peripheral edge portion of the second end wall.

The "outer surface" of the end plate portion refers to a surface facing the opposite side of the space of the one side out of the two widened surfaces of the end plate portion. The "rear surface" of the diaphragm refers to a surface facing the opposite side to the end plate portion of the yoke out of the two surfaces of the diaphragm.

In the electronic valve of this one embodiment, by setting the size of the sealing case from the first end wall to the second end wall to be small, it is possible to have a flattend outer shape along the first and second end walls. Such an outer shape is suitable for mounting the electronic valve (sealing case) along, for example, a wiring board, to form the electronic valve (sealing case) and the wiring board to be totally flattend.

In the electronic valve according to one embodiment, the other end portion of the pole piece provided with the first fluid inlet/outlet is disposed projecting to the outside from the first end wall of the sealing case.

In the electronic valve of this one embodiment, the flow path is easily connected to the first fluid inlet/outlet so as to permit fluid to flow.

In the electronic valve according to one embodiment, the second fluid inlet/outlet is disposed projecting to the outside from the first end wall, the second end wall, or the outer peripheral wall of the sealing case.

In the electronic valve of this one embodiment, the flow path is easily connected to the second fluid inlet/outlet so as to permit fluid to flow. In particular, when the second fluid inlet/outlet is disposed projecting to the outside from the outer peripheral wall of the sealing case, the second fluid inlet/outlet can be prevented from projecting from the second end wall of the sealing case to the outside, and the electronic valve can be formed in thin size. When the second fluid inlet/outlet is disposed projecting to the outside from the first end wall of the sealing case, the second fluid inlet/outlet can be projected in the same direction as the first fluid inlet/outlet. Therefore, for example, a mounting structure can be formed in which the sealing case is mounted on the upper surface of the wiring board, and the second fluid inlet/outlet and the first fluid inlet/outlet are both extended downward through the wiring board.

In an another aspect, a sphygmomanometer of the present disclosure is a sphygmomanometer that measures blood pressure of a part to be measured, the sphygmomanometer comprising:
- a body;
- a cuff attached to the part to be measured;
- a pump mounted in the body and configured to supply fluid to the cuff through a flow path;
- an electronic valve as described above, mounted in the body and interposed between the pump or the flow path and an atmosphere;
- a pressure control unit that controls pressure of the cuff by supplying the fluid to the cuff through the flow path with the pump and/or discharging the fluid from the cuff through the electronic valve; and
- a blood pressure calculation unit that calculates the blood pressure based on pressure of the fluid stored in the cuff.

In the sphygmomanometer of the present disclosure, the body and the cuff are typically attached together to the part to be measured. In this attached state, the pressure control unit controls the pressure of the cuff by supplying fluid to the cuff with the pump through the flow path to pressurize the cuff and/or discharging fluid from the cuff through the electronic valve. The blood pressure calculation unit calculates blood pressure based on the pressure of the fluid stored in the cuff (oscillometric method). In this sphygmomanometer, the electronic valve is made of the electronic valve that can be formed in small size according to the present disclosure. Thus, not only the main body but also the whole of the sphygmomanometer can be formed in small size.

In yet another aspect, an apparatus of the present disclosure is an apparatus capable of measuring blood pressure of a part to be measured, the apparatus comprising:
- a body;
- a cuff attached to the part to be measured;
- a pump mounted in the body and configured to supply fluid to the cuff;
- an electronic valve as described above, mounted in the body;
- a pressure control unit that controls pressure of the cuff by supplying the fluid to the cuff through the electronic valve with the pump and/or discharging the fluid from the cuff; and
- a blood pressure calculation unit that calculates the blood pressure based on pressure of the fluid stored in the cuff.

In the apparatus of the present disclosure, the body and the cuff are typically attached together to the part to be measured. In this attached state, the pressure control unit controls the pressure of the cuff by supplying fluid to the cuff with the pump and/or discharging fluid from the cuff through the electronic valve. The blood pressure calculation unit calculates blood pressure based on the pressure of the fluid stored in the cuff (oscillometric method). In this apparatus, the electronic valve is made of the electronic valve that can be formed in small size according to the present disclosure. Thus, not only the main body but also the whole of the apparatus can be formed in small size.

As is apparent from the above, the electronic valve, the sphygmomanometer, and the apparatus of the present invention can be formed in small size.

The above embodiment is an exemplary, and various modifications can be made without departing from the scope of the present invention. Each of the above embodiments can be implemented independently, but combinations of the embodiments are also possible. In addition, various features in different embodiments can also be independently implemented, but combinations of features in different embodiments are also possible.

The invention claimed is:

1. An electronic valve that permits or blocks a flow of fluid, the electronic valve comprising:
   - a yoke including an end plate portion having an annular peripheral edge, and a side plate portion connected to the peripheral edge of the end plate portion and annularly surrounding a space adjacent to one side of the end plate portion;
   - a pole piece orthogonal to the end plate portion of the yoke and extending in one direction from one end portion existing in the space of the one side to other end portion of opposite side, the pole piece having an opening at the one end portion and having, at the other end portion, a first fluid inlet/outlet in communication with the opening through an inside of the pole piece;
   - a solenoid coil housed in an annular space between the pole piece and the side plate portion of the yoke;
   - a diaphragm made of a disk-shaped magnetic material that faces the end plate portion of the yoke via the space and has a dimension extending over the annular edge of the side plate portion of the yoke;
   - a coil spring that biases the diaphragm in a direction away from the one end portion of the pole piece in a manner of moving the diaphragm translationally in the one direction; and
   - a casing that collectively covers the yoke, a portion of the pole piece extending into the space of the one side, the solenoid coil, the diaphragm, and the coil spring, with the other end portion of the pole piece exposed to an outside,
   wherein
   the coil spring is disposed along an annular space between the side plate portion of the yoke and an annular outer peripheral wall of the casing facing the side plate portion, and is in annular contact with a peripheral edge portion of a surface of the diaphragm facing the end plate portion,
   a gap in a radial direction is provided between the annular outer peripheral wall of the casing and the peripheral edge portion of the diaphragm,
   an elastic body for closing the opening is integrally attached to a portion of the diaphragm facing the opening at the one end portion of the pole piece, and the elastic body has a flat end face projecting in a columnar shape from the diaphragm toward the opening at the one end,
   the pole piece has, at the one end portion, a recess having a flat bottom opened toward the elastic body attached to the diaphragm, and the opening is opened at the bottom of the recess,
   in a non-operating time when the solenoid coil is in an unpowered state, the diaphragm is separated from the one end portion of the pole piece by a biasing force of the coil spring, causing the end face of the elastic body being separated from the opening, such that the electronic valve comes into an open state where the opening is opened, and
   in an operating time when the solenoid coil is in a powered state, the diaphragm approaches the one end portion of the pole piece against the biasing force of the coil spring by a magnetic force generated by the solenoid coil, such that the electronic valve is able to come into a closed state where the opening is closed with the end face of the elastic body.

2. The electronic valve according to claim 1, wherein the pole piece and the yoke are configured integrally.

3. The electronic valve according to claim 1, wherein a magnetic material forming the diaphragm is permalloy.

4. The electronic valve according to any one of claim 1, wherein
    the casing is a sealing case that collectively covers, in a fluid-tight manner, the yoke, a portion of the pole piece extending into the space of the one side, the solenoid coil, the diaphragm, and the coil spring, with the other end portion of the pole piece exposed to an outside; and
    a second fluid inlet/outlet provided through an outer wall of the sealing case.

5. The electronic valve according to claim 4, wherein the sealing case includes
    a first end wall along an outer surface of the end plate portion of the yoke,
    a second end wall along a rear surface of the diaphragm facing an opposite side to the end plate portion, and
    the annular outer peripheral wall connecting a peripheral edge portion of the first end wall and a peripheral edge portion of the second end wall.

6. The electronic valve according to claim 5, wherein the other end portion of the pole piece provided with the first fluid inlet/outlet is disposed projecting to the outside from the first end wall of the sealing case.

7. The electronic valve according to claim 5, wherein the second fluid inlet/outlet is disposed projecting to the outside from the first end wall, the second end wall, or the outer peripheral wall of the sealing case.

8. A sphygmomanometer that measures blood pressure of a part to be measured, the sphygmomanometer comprising:
    a body;
    a cuff attached to the part to be measured;
    a pump mounted in the body and configured to supply fluid to the cuff through a flow path;
    the electronic valve according to claim 1, mounted in the body and interposed between the pump or the flow path and an atmosphere;
    a pressure control unit that controls pressure of the cuff by supplying the fluid to the cuff through the flow path with the pump and/or discharging the fluid from the cuff through the electronic valve; and
    a blood pressure calculation unit that calculates the blood pressure based on pressure of the fluid stored in the cuff.

9. An apparatus capable of measuring blood pressure of a part to be measured, the apparatus comprising:
    a body;
    a cuff attached to the part to be measured;
    a pump mounted in the body and configured to supply fluid to the cuff;
    the electronic valve according to claim 1, mounted in the body;
    a pressure control unit that controls pressure of the cuff by supplying the fluid to the cuff through the electronic valve with the pump and/or discharging the fluid from the cuff; and
    a blood pressure calculation unit that calculates the blood pressure based on pressure of the fluid stored in the cuff.

* * * * *